(12) United States Patent
Parker et al.

(10) Patent No.: US 12,714,355 B2
(45) Date of Patent: Aug. 25, 2026

(54) SYSTEMS AND METHODS FOR PREPARING A NEUROIMAGING SYSTEM FOR NEUROIMAGING AND ANALYSIS OF A SUBJECT'S BRAIN TISSUE

(71) Applicant: COMIND TECHNOLOGIES LIMITED, London (GB)

(72) Inventors: William Parker, London (GB); Pablo Ortega San Miguel, London (GB)

(73) Assignee: Comind Technologies Limited, London (GB)

( * ) Notice: Subject to any disclaimer, the term of this patent is extended or adjusted under 35 U.S.C. 154(b) by 71 days.

(21) Appl. No.: 18/578,481

(22) PCT Filed: Jul. 12, 2022

(86) PCT No.: PCT/GB2022/051810
§ 371 (c)(1),
(2) Date: Jan. 11, 2024

(87) PCT Pub. No.: WO2023/285815
PCT Pub. Date: Jan. 19, 2023

(65) Prior Publication Data

US 2024/0306977 A1 Sep. 19, 2024

(30) Foreign Application Priority Data

Jul. 12, 2021 (GB) ..................................... 2110013

(51) Int. Cl.
*A61B 5/00* (2006.01)

(52) U.S. Cl.
CPC .......... *A61B 5/4064* (2013.01); *A61B 5/0075* (2013.01); *A61B 5/0082* (2013.01); *A61B 5/6844* (2013.01)

(58) Field of Classification Search
CPC ... A61B 5/4064; A61B 5/0075; A61B 5/0082; A61B 5/6844
See application file for complete search history.

(56) References Cited

U.S. PATENT DOCUMENTS

2001/0018554 A1 8/2001 Yamashita et al.
2004/0106856 A1* 6/2004 Kimura ................ A61B 5/0062 250/341.1

(Continued)

FOREIGN PATENT DOCUMENTS

EP 1428471 6/2004
WO 2011/046072 4/2011

(Continued)

OTHER PUBLICATIONS

Pollonini, L., et al., "PHOEBE: a method for real time mapping of optodes-scalp coupling in functional near-infrared spectroscopy," Biomedical Optics Express. vol. 7(12), 2016. p. 5104-5119 (Year: 2016).*

(Continued)

*Primary Examiner* — Sean A Frith
(74) *Attorney, Agent, or Firm* — Barnes & Thornburg

(57) ABSTRACT

A method of preparing a neuroimaging system for neuroimaging and analysis of a subject's brain tissue, the neuroimaging system comprising a plurality of optical elements, wherein each optical element comprises one of: (i) a light source for emitting light towards the subject's brain tissue, or (ii) a light detector for detecting scattered light from the subject's brain tissue, the method comprising: placing optical elements on the subject's scalp to provide at least one source-detector pair where a light source on the subject's scalp is arranged to emit light towards the subject's brain tissue and a detector on the subject's scalp is arranged to detect scattered light from the subject's brain tissue which was emitted from that light source; wherein placing an optical element on the subject's scalp comprises: first, arranging said optical element at a selected location on the subject's scalp for providing at least one source-detector pair; and then, performing an iterative optical element arrangement adjustment process comprising: obtaining a measurement signal indicative of a goodness of fit for said optical element as arranged on the subject's scalp; and re-arranging said optical element at, or proximal to, the selected location on the subject's scalp based on the indication of goodness of fit for said optical element; wherein said iterative optical element arrangement adjustment pro- (Continued)

Figure 1A:
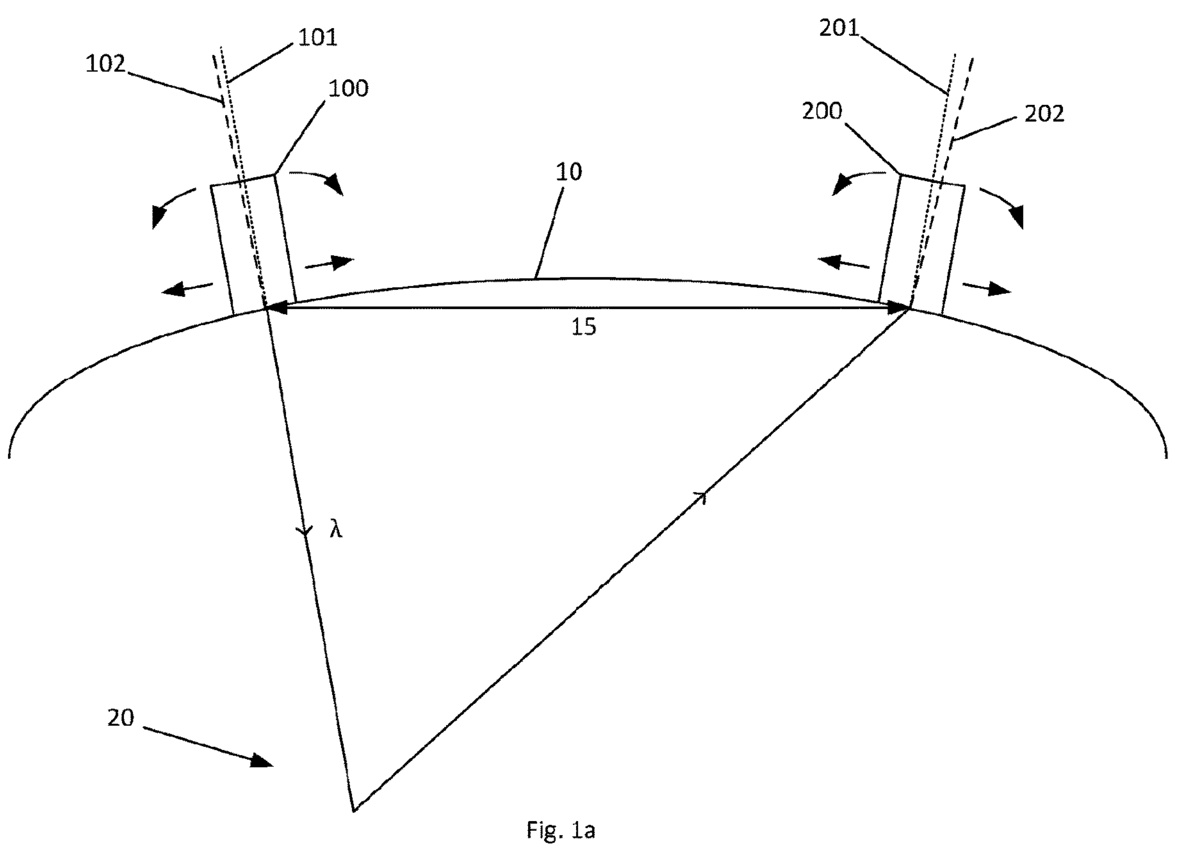

cess is repeated until a said measurement signal indicates a goodness of fit for said optical element which satisfies a threshold criterion.

17 Claims, 5 Drawing Sheets

(56) References Cited

U.S. PATENT DOCUMENTS

2015/0173618 A1 6/2015 Kusukame
2017/0367650 A1 12/2017 Wallois et al.
2018/0345006 A1* 12/2018 Ambrose ............. A61B 5/0536
2019/0183343 A1* 6/2019 Yang .................... A61B 5/0035
2019/0313912 A1* 10/2019 Alford ................... G01N 21/49
2019/0336005 A1 11/2019 Alford et al.
2019/0336006 A1 11/2019 Horstmeyer et al.
2021/0001146 A1 1/2021 Huang
2021/0333308 A1* 10/2021 Franceschini ...... G01R 1/06766
2021/0361209 A1* 11/2021 Young .................. A61B 5/0816

FOREIGN PATENT DOCUMENTS

WO 2016/115392 7/2016
WO 2020/006647 1/2020
WO 2021/216287 10/2021

OTHER PUBLICATIONS

Search Report & Written Opinion issued in PCT/GB2022/051810 (Sep. 19, 2022).
Examination Report issued in GB2110013.6 (Aug. 31, 2021).
Examination Report issued in GB2110013.6 (Mar. 7, 2022).

* cited by examiner

SYSTEMS AND METHODS FOR PREPARING A NEUROIMAGING SYSTEM FOR NEUROIMAGING AND ANALYSIS OF A SUBJECT'S BRAIN TISSUE

CROSS-REFERENCE TO RELATED APPLICATIONS

This application is a US National Stage Application under Section 371 of PCT Application No. PCT/GB2022/051810, filed Jul. 12, 2022, which claims priority from United Kingdom Patent Application No. GB 2110013.6, filed on Jul. 12, 2021, the entirety of each are hereby fully incorporated by reference herein.

TECHNICAL FIELD

The present disclosure relates to the field of Systems and Methods for Preparing a Neuroimaging System for Neuroimaging and Analysis of a Subject's Brain Tissue.

BACKGROUND

Existing neuroimaging techniques include diffuse optical imaging and near-infrared spectroscopy. Such techniques are designed for measuring haemodynamic effects, such as those associated with oxygenation state of haemoglobin in the brain and other effects which manifest in optical absorption characteristics of brain tissue.

These techniques may therefore enable an indication of properties of cerebral blood flow to be obtained. While cerebral blood flow may be used to provide an indication of activity occurring in the brain, cerebral blood flow is an indirect indicator of underlying neuronal activity.

It may be preferable to be able to reliably monitor brain activity in other ways, for example to provide additional and/or alternative information to that which may be obtained by monitoring haemodynamic effects.

SUMMARY

Aspects of the disclosure are set out in the independent claims and optional features are set out in the dependent claims. Aspects of the disclosure may be provided in conjunction with each other, and features of one aspect may be applied to other aspects.

In an aspect, there is provided a method of preparing a neuroimaging system for neuroimaging and analysis of a subject's brain tissue, the neuroimaging system comprising a plurality of optical elements, wherein each optical element comprises one of: (i) a light source for emitting light towards the subject's brain tissue, or (ii) a light detector for detecting scattered light from the subject's brain tissue, the method comprising: placing optical elements on the subject's scalp to provide at least one source-detector pair where a light source on the subject's scalp is arranged to emit light towards the subject's brain tissue and a detector on the subject's scalp is arranged to detect scattered light from the subject's brain tissue which was emitted from that light source. Placing an optical element on the subject's scalp comprises: first, arranging said optical element at a selected location on the subject's scalp for providing at least one source-detector pair; then, performing an iterative optical element arrangement adjustment process comprising: obtaining a measurement signal indicative of a goodness of fit for said optical element as arranged on the subject's scalp; and re-arranging said optical element at, or proximal to, the selected location on the subject's scalp based on the indication of goodness of fit for said optical element; wherein said iterative optical element arrangement adjustment process is repeated until a said measurement signal indicates a goodness of fit for said optical element which satisfies a threshold criterion.

Embodiments may enable the provision of a neuroimaging system having optical elements which are better arranged for obtaining measurements of the subject's brain tissue. Such a neuroimaging system may therefore provide improved neuroimaging and analysis of a subject's brain tissue.

Obtaining a measurement signal indicative of a goodness of fit for an optical element of a source-detector pair may comprise: (i) controlling the light source of the pair to emit a reference light signal, and (ii) controlling the detector of the pair to obtain a reference light detection signal. Said measurement signal indicative of goodness of fit for said optical element of the source-detector pair may be based on the reference light detection signal. Said measurement signal indicative of goodness of fit for said optical element may be based on a signal-to-noise ratio for the reference light signal as identifiable in the reference light detection signal. Satisfying the threshold criterion may comprise said signal-to-noise ratio being greater than a signal threshold value.

Obtaining a said measurement signal for a said optical element may comprise using a sensor to obtain an indication of a property indicating an angular offset between the optical element and the subject's scalp. The angular offset may provide an indication of the pitch/tilt which the optical element makes relative to the subject's scalp. For example, angular offset may provide an indication of how close a scalp-facing surface of the optical element is to running substantially parallel to a region of the scalp which the optical element is facing. The sensor may comprise a capacitance sensor configured to sense a capacitance associated with the optical element and/or the subject's scalp. Satisfying the threshold criterion may comprise sensing a capacitance greater than a capacitance threshold value. The sensor may comprise an impedance sensor configured to sense an impedance associated with the optical element and/or the subject's scalp. The impedance sensor may comprise an RF impedance sensor. Satisfying the threshold criterion may comprise sensing an impedance below an impedance threshold value.

Re-arranging a said optical element may comprise adjusting the pitch of the optical element relative to the subject's scalp and/or translating the optical element to a different location on the subject's scalp. Each optical element may comprise: (i) a scalp facing region for facing the scalp, and (ii) a body (wire/optical fibre) extending away from the scalp facing region. Adjusting the pitch of a said optical element relative to the subject's scalp may comprise changing the pitch of the body of said optical element relative to the subject's scalp. The threshold criterion for a said optical element may be selected based on a goodness of fit for one or more other optical elements arranged on the subject's scalp. The threshold criterion for each said optical element may be selected so that a global goodness of fit for the plurality of optical elements as a whole is greater than a global threshold value. The optical elements may be placed on the subject's scalp to provide a plurality of source-detector pairs, wherein at least one optical element on the subject's scalp may be part of more than one source-detector pair, and wherein the threshold criterion for said at least one optical element may be selected based on the other optical elements in its source detector pairs.

An amount and/or direction of re-arranging for a said optical element may be selected based on the indication of the goodness of fit for said optical element. The amount and/or direction of re-arranging for a said optical element may be selected based on a difference between the indication of goodness of fit in a said measurement signal and the goodness of fit which satisfies the threshold criterion. The threshold criterion for a said optical element may be selected based on the selected location for said optical element. The threshold criterion for a said optical element may be selected based on a determined goodness of fit for other optical elements proximal to said optical element. Each of the plurality of optical elements may be placed on the subject's scalp prior to any iterative optical element arrangement adjustment process occurring. The neuroimaging system for neuroimaging and analysis of a subject's brain tissue may comprise an EROS system and/or an fNIRS system.

The goodness of fit for an optical element may provide an indication of a performance characteristic associated with use of that optical element for neuroimaging and analysis. An optical element may have a goodness of fit which satisfies a threshold criterion if that optical element may be used to obtain measurements having a quality, such as a signal to noise ratio, above a selected level. In other words, the goodness of fit may provide an indication of quality of measurements which could be obtained using that optical element. In some examples, a goodness of fit above a threshold criterion may comprise using the optical element to obtain reference data, and if that reference data is of high enough quality (e.g. signal or signal to noise is above a threshold), then the goodness of fit will satisfy the threshold criterion. In some examples, a goodness of fit being above a threshold value may relate to the quality of a mechanical coupling between the optical element and the scalp. For example, it may be desirable that each optical element couples to the scalp at a selected angle, such as so that a scalp facing region of the optical element lies substantially parallel to a region of the scalp which it faces. A goodness of fit above a threshold value may indicate that the optical element is arranged so that the alignment of these two surfaces (scalp and scalp facing region) is satisfactory (e.g. is close enough to a parallel arrangement, such as above a threshold amount). The goodness of fit for an optical element satisfying the threshold criterion may provide an indication that: (ii) obtained measurements of performance for that optical element in a source-detector coupling are at or above a measurement quality threshold, and/or (ii) obtained measurements of the alignment of a scalp facing region of that optical element relative to a region of the scalp which the optical element is facing is at or above a threshold alignment level.

The iterative optical element adjustment process may be performed by adjusting at least one of: (i) a position, (ii) a tilt, and/or an (iii) absolute contact, for the optical element on the subject's scalp until a measurement signal indicates that the fit satisfies the threshold criterion. In other words, the location of the optical element on the scalp, the angle which the optical element's scalp facing surface makes relative to the scalp, and/or the amount of contact between the optical element's scalp facing surface and the subject's scalp, may be adjusted until the threshold criterion is satisfied. The method may comprise changing the position of the optical element to another position in an area of allowable positions until the threshold criterion is satisfied for a measurement value (e.g. whether the source-detector pair is achieving satisfactory measurement results). The method may comprise changing the angle which the scalp facing surface of the optical element makes relative to the scalp until the threshold criterion is satisfied for a measurement value (e.g. whether the source-detector pair is achieving satisfactory measurement results, and/or whether a sensor indicates that the two are close enough to a selected relative orientation such as being parallel). The method may comprise changing the absolute contact between the scalp facing surface of the optical element and the scalp until the threshold criterion is satisfied for a measurement value (e.g. whether the amount of contact between scalp facing surface and scalp exceeds a satisfactory level).

Performing the iterative optical element arrangement adjustment process may comprise a first step in which at least one of: the optical element is adjusted so that the angle which the scalp facing surface of the optical element makes relative to the scalp satisfies a threshold criterion (e.g. the two are sufficiently parallel), and/or the optical element is adjusted so that the amount of absolute contact between the scalp facing surface of the optical element and the scalp satisfies a threshold criterion (e.g. there is a sufficient amount of absolute contact). The adjustment process may then comprise a second step in which the source-detector pair is operated to obtain a measurement to identify a quality of the arrangement (e.g. to obtain a signal-to-noise value). In the event that the obtained measurement indicates a measurement quality above a threshold value, then the arrangement for the source-detector pair may be finalised, but if not, then the adjustment process may comprise further adjusting location/tilt of the optical element to try to obtain a measurement value which does satisfy the threshold value.

The iterative optical element arrangement adjustment process may be performed automatically using a mechanical actuator configured to obtain each said measurement signal and to re-arrange each said optical element in response to a said measurement signal indicating the goodness of fit for said optical element does not satisfy the threshold criterion.

In an aspect, there is provided a method of neuroimaging and analysing a subject's brain tissue using a neuroimaging system. The method comprises preparing the neuroimaging system as disclosed herein, and controlling operation of the neuroimaging system to provide neuroimaging and analysis of the subject's brain tissue.

In an aspect, there is provided an actuator configured to prepare a neuroimaging system for neuroimaging and analysis of a subject's brain tissue, wherein the neuroimaging system comprises a plurality of optical elements, wherein each optical element comprises one of: (i) a light source for emitting light towards the subject's brain tissue, or (ii) a light detector for detecting scattered light from the subject's brain tissue, wherein: the actuator comprises a plurality of movers, wherein each mover is operable to rearrange one or more optical elements of said neuroimaging system; the actuator is arranged to couple to said neuroimaging system to position the movers proximal to, or in contact with, said optical elements of said neuroimaging system; and the actuator is configured to control operation of each of the movers to re-arrange said optical elements on the subject's scalp.

Each said optical element of said neuroimaging system may comprise: (i) a scalp facing region for facing the scalp, and (ii) a body (such as a wire/optical fibre cable) extending away from the scalp facing region. Each mover may be arranged to move said body relative to the subject's scalp to provide rearrangement of said optical element on the subject's scalp. The actuator may be configured to control operation of each mover to move the body of said optical element to adjust a pitch of said optical element relative to the subject's scalp. The actuator may further comprise at least one contact sensor configured to sense an indication of a contact property for contact between a said optical element and the subject's scalp. The contact sensor may comprise at least one of: (i) a capacitance sensor configured to sense a capacitance associated with said optical element and/or the subject's scalp, and (ii) an impedance sensor configured to sense an impedance associated with said optical element and/or the subject's scalp.

The actuator may be configured to control operation of the one or more movers to perform an iterative optical element arrangement adjustment process for each of said optical elements arranged at respective selected locations on the subject's scalp. To perform said iterative optical element arrangement adjustment process for a light source and/or light detector of a source-detector pair on the patient's scalp, the actuator may be configured to: (i) obtain a measurement signal indicative of a goodness of fit for said optical element as arranged on the subject's scalp; (ii) control operation of one or more of the movers to re-arrange said optical element at, or proximal to, its selected location on the subject's scalp; and repeat steps (i) and (ii) until a said measurement signal is obtained which indicates a goodness of fit for said optical element which satisfies a threshold criterion. At least one optical element may be part of more than one source-detector pair. The actuator may be configured to perform the optical element arrangement adjustment process for said optical element until a threshold criterion is satisfied for that optical element in each of its plurality of source-detector pairs.

The actuator may be configured to obtain a measurement signal indicative of a goodness of a fit for the optical element on the subject's scalp, and to control operation of the one or more movers based on said measurement. For this, the actuator may comprise a controller (such as a microcontroller) configured to receive such a signal and to control operation of the movers accordingly). Additionally, or alternatively, the actuator may comprise analogue circuitry configured to perform such functionality. For example, a closed loop analogue circuit may receive a sensor measurement (such as an indication of a capacitance, impedance etc.), and control operation of the movers accordingly (e.g. to maximise capacitance/minimise impedance etc.).

In an aspect, there is provided an actuator configured to prepare a neuroimaging system for neuroimaging and analysis of a subject's brain tissue, wherein the neuroimaging system comprises a plurality of optical elements, wherein each optical element comprises one of: (i) a light source for emitting light towards the subject's brain tissue, or (ii) a light detector for detecting scattered light from the subject's brain tissue, wherein: the actuator comprises a plurality of movers, wherein each mover is operable to rearrange one or more optical elements of said neuroimaging system; the actuator is arranged to couple to said neuroimaging system to position the movers proximal to, or in contact with, said optical elements of said neuroimaging system; the actuator is configured to control operation of one or more of the movers to place at least one optical element on the subject's scalp to provide a source-detector pair where a light source on the subject's scalp is arranged to emit light towards the subject's brain tissue and a detector on the subject's scalp is arranged to detect scattered light from the subject's brain tissue which was emitted from that light source; and to place an optical element on the subject's scalp, the actuator is configured to: first, control operation of at least one mover to arrange said optical element at a selected location on the subject's scalp for providing at least one source-detector pair; and then, perform an iterative optical element arrangement adjustment process comprising: obtaining a measurement signal indicative of a goodness of fit for said optical element as arranged on the subject's scalp; and controlling operation of at least one mover to rearrange said optical element at, or proximal to, the selected location on the subject's scalp based on the indication of goodness of fit for said optical element; wherein the actuator is configured to repeat said iterative optical element arrangement adjustment process until a said measurement signal indicates a goodness of fit for said optical element which satisfies a threshold criterion.

Each said optical element of said neuroimaging system may comprise: (i) a scalp facing region for facing the scalp, and (ii) a body extending away from the scalp facing region. Each mover may be arranged to move said body relative to the subject's scalp to provide rearrangement of said optical element on the subject's scalp. The actuator may be configured to control operation of each mover to move the body of said optical element to adjust a pitch of said optical element relative to the subject's scalp. The actuator may further comprise at least one contact sensor configured to sense an indication of a contact property for contact between a said optical element and the subject's scalp. The measurement signal indicative of a goodness of fit may contain an indication of a said contact property sensed by the contact sensor. The contact sensor may comprise at least one of: (i) a capacitance sensor configured to sense a capacitance associated with said optical element and/or the subject's scalp, and (ii) an impedance sensor configured to sense an impedance associated with said optical element and/or the subject's scalp. At least one optical element may be part of more than one source-detector pair. The actuator may be configured to perform the iterative optical element arrangement adjustment process for said optical element until a threshold criterion is satisfied for that optical element in each of its plurality of source-detector pairs. The actuator may be configured to perform any of the methods disclosed herein.

In an aspect, there is provided a neuroimaging system comprising: a plurality of optical elements comprising: (i) one or more light sources for emitting light towards a subject's brain tissue; and (ii) one or more light detectors for detecting scattered light from the subject's brain tissue; and an actuator operable to prepare the optical elements of the neuroimaging system for neuroimaging and analysis of the subject's brain tissue. The actuator may comprise an actuator as disclosed herein.

In an aspect, there is provided a computer program product comprising computer program instructions configured to program a controller to perform methods disclosed herein.

FIGURES

Figure 1B:
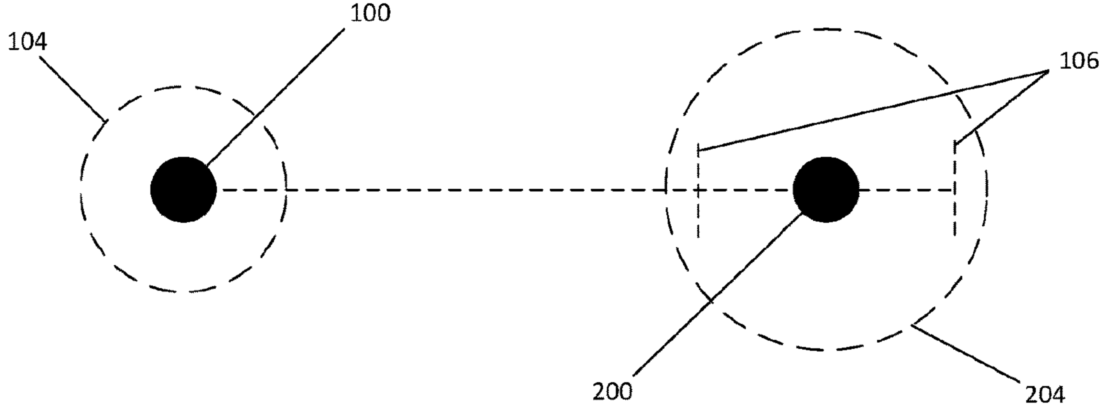

Some examples of the present disclosure will now be described, by way of example only, with reference to the figures, in which:

FIGS. 1*a* and 1*b* are schematic diagrams illustrating an exemplary arrangement of a source and detector of a neuroimaging system in place on a portion of a subject's scalp.

FIGS. 2*a* to 2*e* are schematic diagrams illustrating an exemplary method for preparing a neuroimaging system on a portion of a subject's scalp.

FIGS. 3*a* to 3*e* are schematic diagrams illustrating an exemplary method for preparing a neuroimaging system on a portion of a subject's scalp.

FIGS. 4*a* to 4*f* are schematic diagrams illustrating an exemplary method for preparing a neuroimaging system on a portion of a subject's scalp.

FIGS. 5*a* to 5*f* are schematic diagrams illustrating an exemplary method for preparing a neuroimaging system on a portion of a subject's scalp.

In the drawings like reference numerals are used to indicate like elements.

SPECIFIC DESCRIPTION

Embodiments are directed to systems and methods for preparing a neuroimaging system. The neuroimaging system includes at least one optical source and at least one optical detector, both of which are arranged on a subject's scalp. This provides at least one source-detector pairing for the system (e.g. so that at least one detector of the system may receive light from the subject's brain tissue which originated from one source of the system). An iterative process is used for arranging the one or more sources and/or the one or more detectors on the subject's scalp to provide a satisfactory level. The iterative process involves adjusting the arrangement of sources and/or detectors on the subject's scalp until a satisfactory level of fit is provided for the neuroimaging system on the subject's scalp. The satisfactory level of fit may involve a source and/or a detector being arranged in a desired configuration relative to the surface of the subject's scalp. The satisfactory level of fit may involve the source-detector pairing providing a satisfactory level of signal-to-noise for detecting light at the detector which originated from the light source.

Neuroimaging systems of the present disclosure are configured to direct light towards a subject's brain tissue and to detect resulting scattered light from the subject's brain tissue. Based on this detected light which was directed towards the subject's brain tissue and back scattered therefrom, one or more properties of neural activity within the subject's brain tissue may be inferred. Exemplary neuroimaging systems of the present disclosure include Event Related Optical Signal ('EROS') systems and/or near-infrared systems such as Functional Near-Infrared Spectroscopy ("fNIRS") systems. Examples of such neuroimaging systems will now be described.

Basic Principle of Neuroimaging System

Neuroimaging systems of the present disclosure may direct modulated light to regions of the subject's brain tissue. Light signals caused by scattering of this modulated light from the subject's brain tissue can then be detected by one or more detectors. The light may be amplitude modulated. In which case, the phase of the amplitude modulated waveform carried by the detected light may be used to infer information about the scattering events which scattered the light back towards the detectors. For example, this may provide information about the optical path length from the source to the detector, which can be used to determine the depth in the tissue at which the scattering took place. In other examples, light may be wavelength modulated (e.g. by providing chirped pulses in which the wavelength of emitted light changes). In which case, a wavelength offset between reference light from the light source and detected light from the brain tissue may provide information about the optical path length from the source to detector.

Light Sources

Neuroimaging systems of the present disclosure are arranged to direct light from one or more light sources towards a subject's brain tissue through the scalp and skull. These light sources will typically be positioned on the subject's scalp. The light sources may be configured to provide light which is amplitude modulated with a waveform (e.g. a sinusoid or pulse train). This waveform may be provided from an oscillator connected to the light source. The modulated light from the one or more light sources is directed towards the subject's brain tissue so that it may pass through their scalp, skull and into their brain tissue. It is to be appreciated that the penetration depth of this light may vary depending on a number of factors, such as the wavelength of the light, as well as material properties (e.g. density) of the medium through which the light is passing. Typically, light used in EROS systems of the present disclosure has near-infrared (NIR) wavelengths (e.g. 800 to 2500 nm). At these wavelengths, it can be expected that at least some of the light emitted from the light source will pass into the brain tissue of the subject (i.e. it will not all be blocked by the scalp/skull), and also some of the light will penetrate more deeply into the brain tissue to enable information to be obtained from a greater volume of brain tissue.

Light sources may be configured to provide wavelength modulated light, such as by applying chirped pulses in which the wavelength of light emitted changes (e.g. increases/decreases at a constant rate throughout the duration of one chirped pulse). Some (e.g. the majority) of this light emitted by the source will be directed to the subject's brain tissue for scattering. Some of this light emitted by the source will pass directly to the one or more detectors as reference light (e.g. via an optical cable). The detectors may be configured to combine the reference and detected light to identify a wavelength offset between detected (scattered) light and reference light. The wavelength offset may be used to provide an indication of optical path length (e.g. because it provides an indication of the extra time it took those photons to reach the detector from the light source via the brain tissue (as compared to via the reference path).

Optical Paths of Photons Directed Towards the Subject's Brain Tissue

As light from the one or more light sources passes through the subject's scalp, skull and/or brain tissue, light scattering events will occur as the light interacts with the medium through which it is travelling. It will be appreciated that there may be a plurality of different causes for a scattering event to occur, and the causes for these different scattering events to occur may also depend on properties of the light and/or the medium through which it is travelling. As a consequence of a scattering event, the light will change direction. Photons of light entering the brain tissue will diffuse, moving in random walks due to optical scattering until they are either absorbed or exit the brain tissue. The random nature of this diffusion means that although individual scattered photons have unpredictable paths, bulk photon movements can be accurately understood probabilistically.

The paths followed by masses of photons launched into the brain tissue from one light source and scattered back out onto a photodetector are well understood probabilistically. On average, the trajectories for photons from source to detector are arc-shaped, e.g. a plot of the different trajectories may have a banana shape.

Detectors, and the Spatial Arrangement of the Detectors Relative to the Light Sources The scattering of light within brain tissue and towards a detector will be referred to as 'back scattering of light'. Neuroimaging systems of the present disclosure may utilise one or more light detectors, such as photodiodes, to measure this backscattered light. It will be appreciated that back scattered light will not always travel directly back towards any given location on the scalp, but instead, this light may travel in one of a plurality of different directions (e.g. back scattered light from one light source may be detected at a plurality of different locations on the subject's scalp). Light may be scattered a plurality of times before it reaches a detector. The depth reached by photons emitted from the source and picked up by the detector will be proportional to the distance between the source and detector. For example, short source-detector distances typically cover shallow tissue depths, whereas longer source-detector distances contain photons which travel deeper into the brain tissue. Embodiments of the present disclosure may utilise a plurality of source-detector pairs, each pair being spatially arranged to be associated with a selected depth of light penetration into the subject's brain.

Some of the back scattered light signals may carry information about activity occurring within the brain. The detectors may be operable to determine one or more properties of the back scattered light which they detect. The system may be configured to determine an indication of: (i) the intensity of light incident on the detector, (ii) phase information associated with light incident on the detector-such phase information may be provided by the phase of the waveform carried as amplitude modulation on the scattered light, and/or (iii) a wavelength offset between light incident on the detector and reference light which travelled directly to the detector from the light source. This information may be used to identify a time of flight ('TOF') for photons. For example, phase information in detected light may be used to provide an indication of the temporal offset of that light as compared to light which would have reached the detector along a path of known length. This difference in phase (and thus difference in time of flight from source to detector) will provide an indication of the distance that photon has travelled to get from the source to detector (e.g. its optical path length). Similar comments apply to detecting wavelength offsets to reference light. Neuroimaging systems of the present disclosure may utilise probabilistic models to estimate the photon path from source to detector, and/or the penetration depth of that photon within the brain tissue based on this information.

Neuroimaging and Analysis Based on Detected Signals

EROS systems of the present disclosure may be configured to detect an indication of fast optical signals ('FOS') occurring in the subject's brain tissue. These fast optical signals relate to neural activity, such activity can cause changes in optical scattering properties of the brain tissue in which that activity occurs. As such, scattering properties of light in brain tissue will vary concurrently with neural activity in that brain tissue, and so an indication of the neural activity occurring may be obtained based on information contained within scattered light signals measured by detectors. The physiological mechanisms responsible for such fast optical signals comprise cell swelling and membrane conformation changes. These changes may occur during the transfer of ions and water that happen during electrical neuronal events such as action potentials in the brain.

As a result of the fast optical signals occurring (or not occurring), different regions within the brain tissue will cause light scattering events at different rates. For example, when a region of the brain is active (e.g. when fast optical signals are being transmitted through that region of the brain), the activity in that region will lead to a different number and/or type of scattering events occurring, as compared to a region which is dormant (e.g. when no, or not many, fast optical signals are being transmitted through that region of the brain). This will be evident in properties of the measured signals, such as phase offsets, as either a change in phase offsets will indicate an event occurring (e.g. which caused the scattering to occur), or an absolute value of the phase offset itself will indicate a depth at which an event (e.g. a scattering) occurred. Similar comments apply to wavelength offsets.

Near Infrared Systems of the present disclosure, such as fNIRS systems, may apply similar principals for determining time of flight/optical path lengths for detected photons which originated from the light source and scattered in the subject's brain tissue to the detector. For these systems, the scattering of light may be governed by haemodynamic effects occurring with the subject's brain tissue. For example, due to the flow of blood, properties of scattering events may change. As a result, a change in optical path length may provide an indication of a change in blood flow to a region along that optical path.

Temporal Monitoring/Temporal Neuroimaging and Analysis

Neuroimaging systems of the present disclosure may be configured to repeatedly (e.g. continuously) pass photons from the one or more light sources through intervening brain tissue to detectors of the system. By monitoring properties of the back scattered light received at the one or more detectors, systems of the present disclosure may determine whether any neural events are occurring (e.g. whether the detected signals correspond to regions of the brain through which fast optical signals are being transmitted). For example, neural activity in a volume of brain tissue may be inferred based on a change in the rate of scattering of light associated with that volume of brain tissue (e.g. light which has passed through that volume of brain tissue). Neuroimaging systems of the present disclosure may utilise a plurality of different source-detector pairs arranged to enable activity in different regions of the brain to be monitored at the same time.

By monitoring lots of detected photons, and having an estimate for their expected trajectories through the brain tissue, changes in neural activity may be identified based on measured phase offsets at the detector. For example, where a source-detector pair initially receives photons having a consistent phase offset (and thus consistent time of flight), and then photons are suddenly received having less of a phase offset (e.g. indicating a smaller time of flight), this may suggest that neural activity has occurred somewhere on that expected trajectory causing earlier scattering than expected. Based on this shorter time of flight, an indication of penetration depth for the scattering event may be determined, and this provides an indication of activity in a certain region of the brain tissue. Using these probabilistic methods, it is possible to filter out photons which did not reach the brain tissue, as these will have probabilistically travelled shorter paths from their source to a detector.

Embodiments of the present disclosure relate to systems and methods for preparing a neuroimaging system for neuroimaging and analysis of a subject's brain tissue.

A first example of a neuroimaging system, and its arrangement on a subject's scalp, will now be described with reference to FIGS. 1*a* and 1*b*.

FIG. 1*a* shows a neuroimaging system in place on a subject's scalp 10. The neuroimaging system comprises two optical elements: light source 100 and light detector 200. The light source 100 and light provide one source-detector pair.

To illustrate the arrangement of the optical elements on the subject's scalp 10, an exemplary light path is show from the light source 100 to a scattering region 20 where the light is scattered to the light detector 200. Light from the light source 100 is emitted at a wavelength A. Also shown is an indicator of a separation distance 15 for the distance of separation between the light source 100 and light detector 200. The distance of separation could be a birds-eye view of the separation distance, a distance along the surface of the scalp 10, and/or an optical path distance (e.g. average distance) from source 100 to detector 200.

Also shown is a light source angle line 101, a light detector angle line 201, a light source normal line 102 and a light detector normal line 202. The light source angle line 101 runs perpendicular to the region of the light source 100 in contact with the scalp 10. The light detector angle line 201 runs perpendicular to the region of the light detector 200 in contact with the scalp 10. The light source normal line 102 runs orthogonal to the scalp surface in the region in which the light source 100 is coupled to the scalp 10. The light detector 200 normal line 202 runs orthogonal to the scalp surface in the region in which the light detector 200 is coupled to the scalp 10. These lines are included to illustrate the angles which the light source 100 and detector 200 make relative to the scalp 10, and how these angles compare to being arranged orthogonal to the scalp 10. As can be seen, neither the light source 100 nor the light detector 200 lies perpendicular to the scalp surface. The light source 100 is closer to perpendicular than the light detector 200.

The light source 100 has a scalp facing region and a body extending away from the scalp facing region. The scalp facing region is placed close to, or in contact with, the scalp 10. The light source 100 is provided at a first region on the subject's scalp 10. The arrows around the light source 100 indicate potential directions of movement for the light source 100. These are to translate the light source 100 (e.g. move it to a different location on the scalp 10) and/or to tilt the light source 100 (e.g. to change the angle it makes relative to the scalp surface). The light source 100 may comprise an optical fibre for coupling for directing light to the scalp 10 at the scalp facing region of the light source 100.

The light detector 200 is spaced away from the light source 100 on the scalp 10. The light detector 200 has a scalp facing region and a body extending away from the scalp facing region. The scalp facing region is placed close to, or in contact with, the scalp 10. The light detector 200 is provided at a second region on the subject's scalp 10 (different to the first region). The arrows around the light detector 200 indicate potential directions of movement for the light detector 200. These are to translate the light detector 200 (e.g. move it to a different location on the scalp 10) and/or to tilt the light detector 200 (e.g. to change the angle it makes relative to the scalp surface). The light detector 200 may comprise an optical fibre for coupling for directing light away from the scalp 10 at the scalp facing region of the light detector 200.

The light source 100 is arranged to emit light at wavelength A which is directed towards the scattering region 20. The light detector 200 is arranged to detect light incident on a detection surface thereof. The incident light may include scattered light which originated from the first light source 100. The light source 100 and light detector 200 are arranged to provide a source-detector pair. For example, the light source 100 and detector 200 are positioned (e.g. located and/or angled) to enable some (e.g. more than a threshold amount) of light emitted from the source 100 to be detected at the detector 200. In examples where the detector 200 is configured to detect a wavelength offset between scattered light and reference light, the light detector 200 may be coupled to the light source 100 to receive reference light therefrom. The light source 100 is configured to determine one or more properties of incident light received on its detection surface, such as a phase/wavelength offset, and/or intensity profile. Based on this information, one or more properties of neural activity may be inferred.

Embodiments are directed at systems and methods for improving the arrangement of the light source 100 and light detector 200 on the subject's scalp 10. This may enable greater measurement accuracy and/or precision to be obtained. For example, by providing a better arrangement of the optical elements on the subject's scalp 10, more information and/or more reliable information may be obtained for the same amount of light being directed from the light source 100 towards the subject's brain tissue.

FIG. 1*b* illustrates some exemplary constraints to be used when improving the arrangement of optical elements on a subject's scalp 10.

FIG. 1*b* shows a plan view of the arrangement shown in FIG. 1*a*. The light source 100 and the light detector 200 are shown as black filled circles. FIG. 1*a* also shows a light source allowable location region 104 and a light detector allowable location region 204. These regions are shown as circles surrounding the optical element, but it is to be appreciated that the region need not be circular, nor need it be centred on the current location of the optical element. Also shown is an allowable source-detector separation distance 106. This separation distance is shown to be bounded by two parallel straight lines although it is to be appreciated that the boundaries need not be straight or parallel. For example, the separation distance may trace an annular region (or at least partially annular region).

Each optical element may have an associated intended function and/or region of interest. That is, each source/detector may be arranged to obtain a particular type of information from the subject's brain tissue, and/or to obtain information from a particular region of the subject's brain tissue. In order to obtain such information for a given optical element, constraints may be placed on the location on the subject's scalp 10 for that optical element. For example, if a source-detector pair is intended to obtain information from a region towards the front of the subject's brain, then the source 100 and detector 200 will need to be placed on the scalp 10 towards the front side of the subject's brain. An allowable region may thus be defined for a given optical element. The allowable region may be a region on the subject's scalp 10 where that optical element may be placed in order to enable it to obtain desired information from the subject's brain tissue. For high precision elements (e.g. for specific information associated with a particular region of the brain), the selected region may be small, whereas the selected region may be lower for lower precision elements. In the example of one source and one detector 200, the selected region will be specific to just the one source/detector. However, it is to be appreciated that if there are a plurality of sources/detectors, the same region may apply to many of them.

Regions 104 and 204 in FIG. 1*b* illustrate the allowable regions for the source 100 and detector 200 respectively. As can be seen, the allowable region 204 for the detector 200 may be bigger than that for the source 100. Information may be stored which defines the boundaries of the allowable region for each of the light source 100 and/or the detector 200. In this sense, the location for the light source 100 may be deemed acceptable as long as it is within its allowable region 104, and/or the location for the light detector 200 may be deemed acceptable as long as it is within its allowable region 204.

Each source-detector pair may be associated with a selected optical path length and/or penetration depth into the subject's brain tissue. The deeper photons penetrate into the brain tissue before scattering, the further away the detectors should be from the source 100. For example, a light detector right next to a light source on the scalp 10 may detect a lot of photons which originated from the light source. However, these are likely to be photons which scattered immediately (e.g. from contact with scalp/skull rather than brain tissue), and so they will carry limited information as to properties of the subject's brain tissue. Likewise, if a light detector is arranged too far away from the light source 100 on the scalp 10, it may not detect any photons from the light source 100 (e.g. the two may not provide a source-detector pair).

The allowable source-detector separation distance shown in FIG. 1*b* illustrates an example of a selected range for separation between the source 100 and detector 200. Information may be stored for each source-detector pair which stipulates a range of allowable separation distances between the source 100 and detector 200. In this sense, the arrangement of light source 100 and light detector 200 on the scalp 10 may be deemed acceptable if the two are within the allowable separation range from each other.

The allowable location regions and allowable separation distances represent two possible constraints which may be used when arranging optical elements on the subject's brain. Additionally, or alternatively, other constraints could also be used.

An exemplary method of improving the arrangement of the optical elements on the subject's scalp 10 will now be described with reference to FIGS. 2*a* to 2*e*.

Figures 2A, 2B, 2C, 2D, 2E:
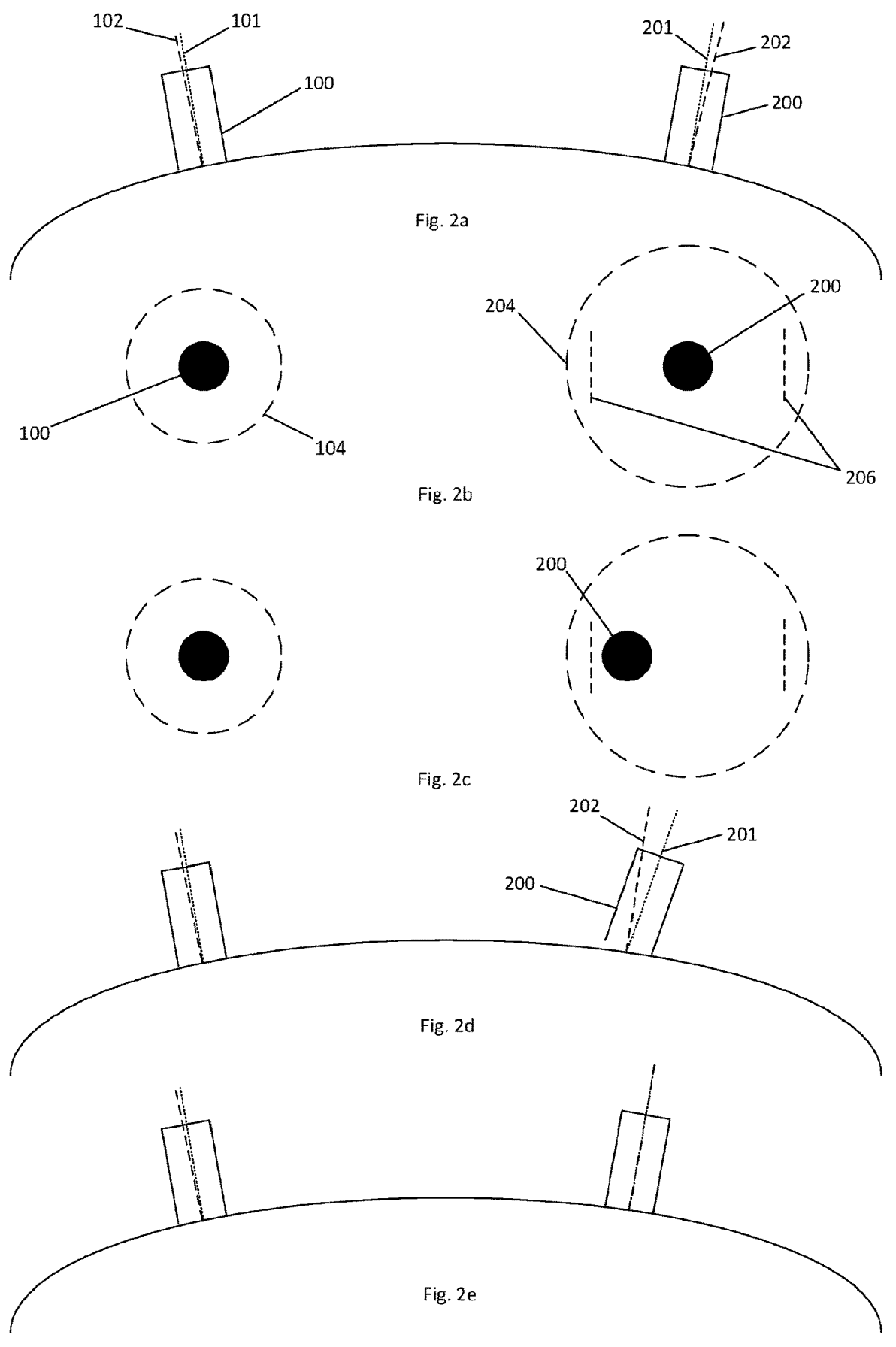

FIGS. 2*a* and 2*b* show a similar arrangement to that of FIGS. 1*a* and 1*b*. That is, the optical elements are arranged on the scalp 10 in an initial configuration. For example, they may have just been placed on the subject's scalp 10. The method involves improving this arrangement of the optical elements on the scalp 10. As with FIG. 1*b*, allowable regions are shown for the source 100 and detector 200, as is an allowable range for the separation distance between the two.

With the optical elements arranged in their initial configuration (as shown in FIG. 2*b*), one or more measurement signals are obtained to adjust the arrangement of the detector 200. This involves an iterative optical element arrangement adjustment process. As a first step, with the optical elements in their initial configuration, the light source 100 is operated to emit light towards the subject's brain tissue, and the detector 200 is operated to detect scattered light from the subject's brain tissue which originated from the light source 100. The light may be emitted according to a selected pattern for reference light. For example, the light may be emitted with a selected modulation scheme applied thereto for detection by the detector 200.

The detector 200 is operated to try to detect this reference light signal. Based on the photons incident on a detection surface, the reference light signal may be detected. For instance, an intensity/number/wavelength of incident photons on the detection surface may fluctuate over time based at least in part on a modulation pattern applied by the light source 100. Thus, the presence of the reference signal may be detected in the obtained measurement signal. Based on this, a metric may be determined which provides an indication of the quality of the arrangement of the detector 200 on the scalp 10 (e.g. a goodness of fit for the source-detector coupling on the scalp 10). The metric may be based on a magnitude of the intensity/number of photons incident on the detection surface and/or it may be based on the signal to noise ratio for the reference signal as identifiable in the detected signal.

Once the metric has been obtained, the arrangement of at least one of the optical elements is varied. In this example, the position of the light detector 200 on the subject's scalp 10 is changed. The process is iterated by first moving the light detector 200 to a different location, and then obtaining the metric for the light detector 200 in that different location. The direction of movement of the light detector 200 may be guided based on a change in value for the metric. For example, if movement in one direction yields a worse metric value than the previous position, the new position for the light detector 200 may be selected by moving the light detector 200 in a different direction away from that previous position. The amount of change in position may also be controlled based on obtained metrics. For example, the further away an obtained metric is from satisfying the threshold criterion, the further the light detector 200 may be moved from that position. A plurality of different positions may be tried, and respective metrics obtained for those positions, before a suitable position is identified. The positions which are tried are based on the constraints applied for the optical elements. For instance, with reference to FIG. 2*b*, the detector 200 position may be moved to different positions within the area which intersects the light detector allowable region 204 and the source-detector allowable separation distance 206.

This iterative process is repeated until a threshold criterion is achieved. The threshold criterion may be a relative measure or an objective measure and/or it may be based on a number of iterations tried. For example, once the metric indicates a goodness of fit above a threshold value, that position may be adopted (e.g. without trying further positions). It may be that the threshold value changes in dependence on the number of iterations tried (e.g. so that the goodness of fit threshold value drops as more iterations are tried). It may be that after a selected amount of time/number of iterations, the position with the best metric is adopted. In any case, once the threshold criterion is achieved, the light detector 200 is moved into a new configuration in which the light detector 200 is placed in the position which satisfied the threshold criterion. This arrangement is shown in FIG. 2*c*. A can be seen, the light detector 200 has moved slightly closer to the light source 100, but it is still within its allowable location region 204 and separation distance 206.

In this example, the position of the light detector 200 is iterated until the threshold criterion is satisfied. Then, no further position changes are performed for the light detector 200. The angle which the light detector 200 makes relative to the subject's scalp 10 may then be adjusted.

FIGS. 2*c* and 2*d* show the arrangement of the optical elements on the scalp 10 after the light detector's position has been iteratively adjusted to provide an improved location of the detector 200 on the scalp 10. As can be seen in FIG. 2*d*, the angle of the light detector 200 relative to the scalp 10 is away from being orthogonal to the scalp 10. The method further comprises adjusting the angle which the light detector 200 makes to the scalp 10 to provide improved measurements.

Each optical element comprises a scalp-facing region and a body extending away from the scalp-facing region. Adjusting the pitch which the light detector 200 makes relative to the scalp 10 may comprise moving the body of the element thereby to pivot the element relative to the scalp-facing region. Adjusting the angle which an optical element makes to the surface of the scalp 10 may comprise an iterative process in which the angle is changed, and a measurement process is performed to identify a goodness of fit for the detector 200 at its changed angle. This process may be repeated until a goodness of fit for the detector angle satisfies a threshold criterion (similar to the approach described above in relation to the position of the detector).

One or more measurements may be obtained to determine a goodness of fit for the angle of the detector 200. Such measurements may provide an indication of the angle which the light detector 200 makes relative to the scalp 10 and/or an indication of quality for a measurement signal being detected (e.g. in the manner described above in relation to reference light signal measurement for adjusting the position of the detector 200 on the scalp 10).

To determine an indication of an angle of the detector 200 relative to the scalp 10, one or more sensors may be provided. For example, an electronic sensor, such as an impedance sensor or a capacitance sensor may be provided. It is to be appreciated in the context of the present disclosure that the angle which the sensor makes relative to the scalp 10 will influence electrical properties between those two.

For example, the capacitance between a scalp-facing surface of the detector 200 and the scalp 10 may provide an indication of how close the detector 200 is to the scalp 10. In turn, this may provide an indication of the angle which the detector 200 makes to the scalp 10. A larger capacitance will be present when the surface which faces the scalp 10 is located closer to the scalp 10, e.g. where that surface and the scalp 10 are in parallel planes (and located close to each other). Thus, by measuring an indication of this capacitance, an indication of the angle which the detector 200 makes relative to the scalp 10 may be obtained. To provide an improved angle of the detector 200 relative to the scalp 10, the detector's pitch may be adjusted so that the scalp-facing surface of the detector 200 runs closer to parallel with the scalp 10. In the example shown in the Figs., the detector 200 is right-angled in shape, and so the detector 200 will extend orthogonally away from the scalp 10 when the scalp-facing surface of the detector 200 runs parallel to the scalp 10.

For similar reasons, the impedance associated with one or both of the scalp-facing surface of the detector 200 and the scalp 10 in that region may provide an indication of the relative angular offset between the plane of the scalp 10 and the plane of the scalp-facing surface of the detector 200. A larger impedance will indicate a less good fit. An impedance sensor, such as an RF impedance sensor, may be used to obtain and indication of said impedance. Thus, by measuring an indication of impedance, an indication of the angle which the detector 200 makes relative to the scalp 10 may be obtained. To provide an improved angle of the detector 200 relative to the scalp 10, the detector's pitch may be adjusted so that the scalp-facing surface of the detector 200 runs closer to parallel with the scalp 10.

A plurality of sensors may be provided to indicate how properties may vary in different locations. For example, for impedance sensing, a plurality of impedance sensing pins may be provided, or a ring sensor may be provided which extends around the optical element. A similar arrangement of capacitance sensors may be provided, and/or a plurality of mechanical sensors may be provided. By utilising a plurality of sensors distributed about the optical element, differences in sensor values may be monitored. For example, an indication that e.g. impedance or capacitance, varies in different regions, an indication of tilt for the optical element may be determined. For example, if it is identified that one region of optical element is closer to the scalp than another, an indication of tilt of the optical element relative to the scalp may be determined. A similar approach may be provided using mechanical sensors, such as to provide a mechanical tilt measurement. For example, a plurality of legs may couple the optical element to the scalp, and the sensors may provide an indication of force, extension, strain etc. of each leg, may enable tilt to be determined. As another example, a quadrant position sensor, such as a quadrant position photodiode sensor, could be used.

By providing a plurality of distributed contact sensors for an optical element, e.g. which surround a scalp contacting surface of the optical element, measurements from one region relative to measurements from another region may be utilised to determine an indication of tilt of the optical element relative to the scalp. Additionally, or alternatively, a magnitude of sensor measurements may be utilised to indicate how closely coupled to the scalp the optical element is. For example, this may provide an indication of absolute contact between optical element (scalp-contacting surface) and the scalp itself.

In some examples, an absolute contact or tilt measurement may be performed first. For example, an indication of tilt or contact for an optical element may be obtained, and the arrangement of that optical element controlled so that the absolute contact and/or tilt satisfies a selected criterion. After this, measurements may be obtained to determine if the optical element provided a desired signal to noise ratio. If it did, then the arrangement may be deemed optimised. If it did not, then the location and/or tilt of the optical element may be controlled to increase the signal to noise ratio.

As another example, the tilt of the detector 200 may be varied, and the detector 200 operated to obtain a measurement signal for identifying reference light from the light source 100 (e.g. in the manner described above for position). In which case, a tilt angle for the detector 200 which results in a better measurement value (e.g. better signal to noise ratio) may be used for indicating a preferred tilt relative to the scalp 10.

The tilt of the detector 200 may be varied then measurements obtained for that tilt iteratively. In other words, the tilt may be changed, a measurement obtained for that tilt angle, and then the tilt angle is further changed until a resulting measurement satisfies a threshold criterion. The approach for satisfying the threshold criterion may be the same as described above for the position of the detector 200. For example, once a capacitance value above a threshold level (absolute/relative), an impedance value below a threshold level (absolute/relative), and/or a reference signal detection measurement at above a threshold level (absolute/relative) is obtained, the process is stopped and that particular tilt angle is adopted for the light detector 200.

A final arrangement may then be taken for the optical elements. This is shown in FIG. 2*e*, where the final position for the light detector 200 is that which was identified in step FIG. 2*c*, and a tilt for the light detector 200 relative to the scalp 10 in that position has been finalised. As can be seen in the example of FIG. 2*e*, the scalp-facing surface of the detector 200 is substantially parallel to the scalp 10 (and the detector 200 extends orthogonally away from the scalp 10).

The arrangement for the optical elements (the source 100 and detector 200) are then taken as finalised. The neuroimaging system, as finalised, is then used to obtain measurements of neural activity, e.g. by emitting light from the light source 100 and detecting scattered light at the detector 200.

The above-described method optimises optical element arrangement based on both the positioning of optical elements on the scalp 10, and also the angle which those elements make relative to the scalp 10. In this method, the position is first optimised, and then the tilt is subsequently optimised. This method is also based on optimising the detector 200 arrangement for a fixed source arrangement. However, it will be appreciated that these features should not be considered limiting. For example, the method need not arrange both positioning and angle of elements on the scalp 10, nor need the method be performed in the described order (e.g. location before tilt). The position and tilt may be adjusted together (e.g. move to new position, improve tilt in that position, obtain final measurement for that position, then move to new position and repat). As another example, the method may instead be based on optimising the source arrangement for a fixed detector 200 and/or optimising both source 100 and detector 200.

Additionally, the above example relates to a neuroimaging system with only one light source 100 and only one light detector 200. However, the present disclosure extends to more arrangements, such as for neuroimaging systems with a plurality of light sources and light detectors. Exemplary methods for preparing such neuroimaging systems will now be described with reference to FIGS. 3, 4 and 5.

FIGS. 3*a* to 3*e* show an exemplary method of arranging multiple optical elements on a subject's scalp 10.

Figures 3A, 3B, 3C, 3D, 3E:
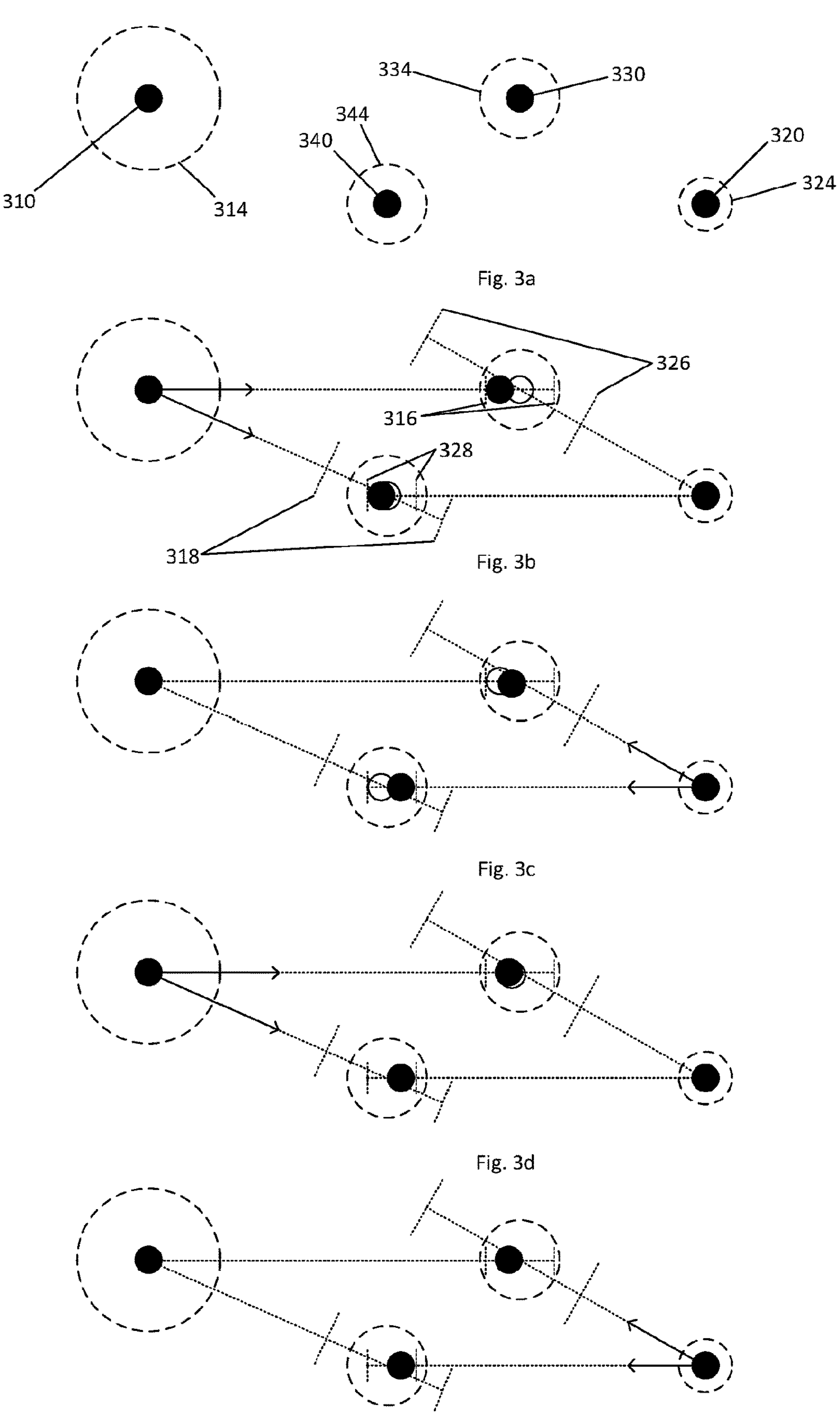

FIG. 3*a* shows an arrangement of optical elements on a subject's scalp. This arrangement is a multi-source and multi-detector arrangement including a first light source 310, a second light source 320, a first light detector 330, and a second light detector 340. The optical elements are all spaced apart from each other on the subject's scalp. In this example, location-based constraints are provided for each element on the subject' scalp. As shown, there is a first light source allowable region 314, a second light source allowable region 324, a first light detector allowable region 334, and a second light detector allowable region 344. As with the earlier example, these regions define allowable locations on the subject's scalp for placement of the optical elements. The arrangement of the optical elements will be optimised subject to a constraint that the optical elements must each remain within their allowable region. In this example, all of the elements have such regions defined, but it will be appreciated that this need not be the case, and instead only some (or none) of the elements may have such allowable regions defined.

In this example, the arrangement of detectors will be optimised iteratively for different light sources. In other words, the sources may not be rearranged, but the detectors will be, to provide an improved arrangement of the detectors relative to the sources. Each of the detectors provides a source-detector pair with each of the sources. In other words, there are four source-detector pairs provided (first source-first detector; first source-second detector; second source-first detector; second source-second detector). For each pair, the optical elements are arranged to enable the light detector to obtain signal data from the light source.

In addition to the example with only one source-detector pair, different source-detector pairs in this example may be attributed different levels of importance. For example, certain source-detector pairs may be arranged to detect specific signals (e.g. from specific regions of the brain), which may be more useful/important than for others. For example, it may be beneficial to obtain a good spread of coverage for the brain tissue. Some pairs may be prioritised to ensure a good spread of coverage.

As with the earlier example, a range of allowable separation distance values may be defined for one or more of the source detector couplings. This is shown in FIG. 3*b*, which indicates four such ranges: (i) first detector-first source allowable separation distance range 316, (ii) first detector-second source allowable separation distance range 318, (iii) second detector-first source allowable separation distance range 326, (ii) second detector-second source allowable separation distance range 328.

The example of FIGS. 3*a* to 3*e* is similar to the example of FIGS. 2*a* to 2*e* in the sense that the arrangement of detectors on the scalp can be optimised using these two sets of constraints (optical element position constraints and source-detector pair separation distance constraints). However, unlike the example of FIGS. 2*a* to 2*e*, there are additional source-detector pairs for optimising, and optimising one pair may influence the arrangement of the other pair. As a result, the method involves an iterative process in which the optimisation is performed for different pairs iteratively until a global level of fit exceeds a threshold criterion (as opposed to a local level of fit for one pair per se.).

In FIG. 3*b*, the first and second detector positions are optimised for the first light source 310 (the arrows from the light sources in FIGS. 3*b* to 3*e* indicate which light source is being optimised). For the detectors, the filled black circles indicate the new position and the non-filled black circles indicate the previous position. Each of the first and second detect is moved to provide improved operation with the first light source 310. As can be seen, they have each moved towards the first light source 310. This process may be iterative, as with the example of FIGS. 2*a* to 2*e*, in that different positions may be tried for the detectors, and the process repeated until a suitable position for each detector is identified (within the constraints).

To control the optimisation process, different levels of constraint may be placed on different optical elements/source-detector pairs. For instance, stored information about the constraints may be used when optimising. This stored information may also include one or more weightings which stipulate the importance of the performance of individual source-detector pairs. For example, the weightings may provide an indication of prioritisation for optimising the different pairs (e.g. to indicate which pairs should be prioritised when arranging elements, and by how much they should be prioritised). Additionally, or alternatively, identifying which pairs to prioritise may be enforced using the constraints described above. For example, as can be seen in FIG. 3*b*, the most finely tuned of the pairs will be the second source-second detector pair, followed by the first source-first detector pair. The other pairs can be much less finely tuned, as their constraints are much more relaxed.

FIG. 3*c* shows a second stage in the iterative optical element arrangement adjustment process. This time, the arrangement of detectors is optimised for the second light source 320. As such, the detectors are each moved into a position which provides a better pairing with the second light source 320. In so doing, information about the pairing with the first light source 310 may be used. For example, measurements obtained during the first re-arrangement step with the first light source 310 may be used to limit subsequent movements of the detectors. In FIG. 3*c*, both detectors have moved to closer to the second light source 320.

The first detector 330 is prioritised more towards its pairing with the first light source 310. As a result, the amount by which it moves for optimisation to the second light source 320 is limited somewhat. For instance, measurement values obtained when optimising the first light detector 330 to the first light source 310 may be used, as well as new measurement values obtained when optimising the first detector 330 to the second light source 320. With a plurality of such measurement values, a compromise location may be selected for the first detector 330. This location may be the one which provides desired operational characteristics across both light sources. For example, this may involve using an importance weighting for each of the two pairings, so that the compromised location may achieve the best position for the two pairings which also considers the respective importance of the two pairings. As shown in FIG. 3*c*, the first detector 330 only moves a small way towards the second light source 320. The best position for the detector for the second light source 320 may be much closer to the second light source 320, but the compromised position is one between the two extremes (the first extreme being the best location for the first light source 310 and the second extreme being the best location for the second light source 320). The amount by which the first detector 330 moves between the two extremes may be controlled as per the importance of the two pairings. In this case, the first source-first detector pairing is more important, and so the position of the first detector 330 is biased more towards its optimised position for the first light source 310 than an optimised position for the second light source 320. In this sense, the first detector 330 is arranged in a position which satisfies a global threshold criterion (based on both light sources).

The second detector 340 may also be optimised in a similar manner to the first detector 330. In this example, the second source-second detector pairing is significantly more important than the first source-second detector pairing. As such, the position of the second light detector 340 is based predominantly on its optimisation for the second light source 320. In FIG. 3*c*, it has moved quite far towards the second light source 320 (within its constraints). Even though this movement will reduce the quality of its first light source pairing, this approach is taken as the weighted combination of the two pairing qualities will be increase (e.g. maximised). This may then satisfy a global threshold criterion for the second light detector 340.

FIGS. 3*d* and 3*e* show further steps in the iterative optical element arrangement adjustment process. These steps may comprise validation steps to confirm that the re-arranging of the optical elements in the previous steps has led to an arrangement which satisfies the relevant threshold criteria. These steps may also comprise additional rearranging of the optical elements. In FIG. 3*d*, a small change is made to the first detector's position to improve its pairing with the first light source 310, but no change is made to the second detector's position. In FIG. 3*e*, no changes are made to either detector's position. The arrangement is therefore deemed optimised, as the collective performance of the four source-detector satisfies a threshold criterion (e.g. the collective performance has been maximised). This may be taking into account the respective importance of individual source-detector pairings.

FIGS. 4*a* to 4*f* show steps of a method for arranging optical elements on a subject's scalp. This method follows a similar approach to that of FIGS. 3*a* to 3*e*, but the tilt of the individual elements may be varied. This method of FIGS. 4*a* to 4*f* may be performed after the method of FIGS. 3*a* to 3*e*, it may be performed in combination with (e.g. interspersed with) the method of FIGS. 3*a* to 3*e*, or it may be performed separately (e.g. without performing the method of FIGS. 3*a* to 3*e*).

Figures 4A, 4B, 4C, 4D, 4E, 4F:
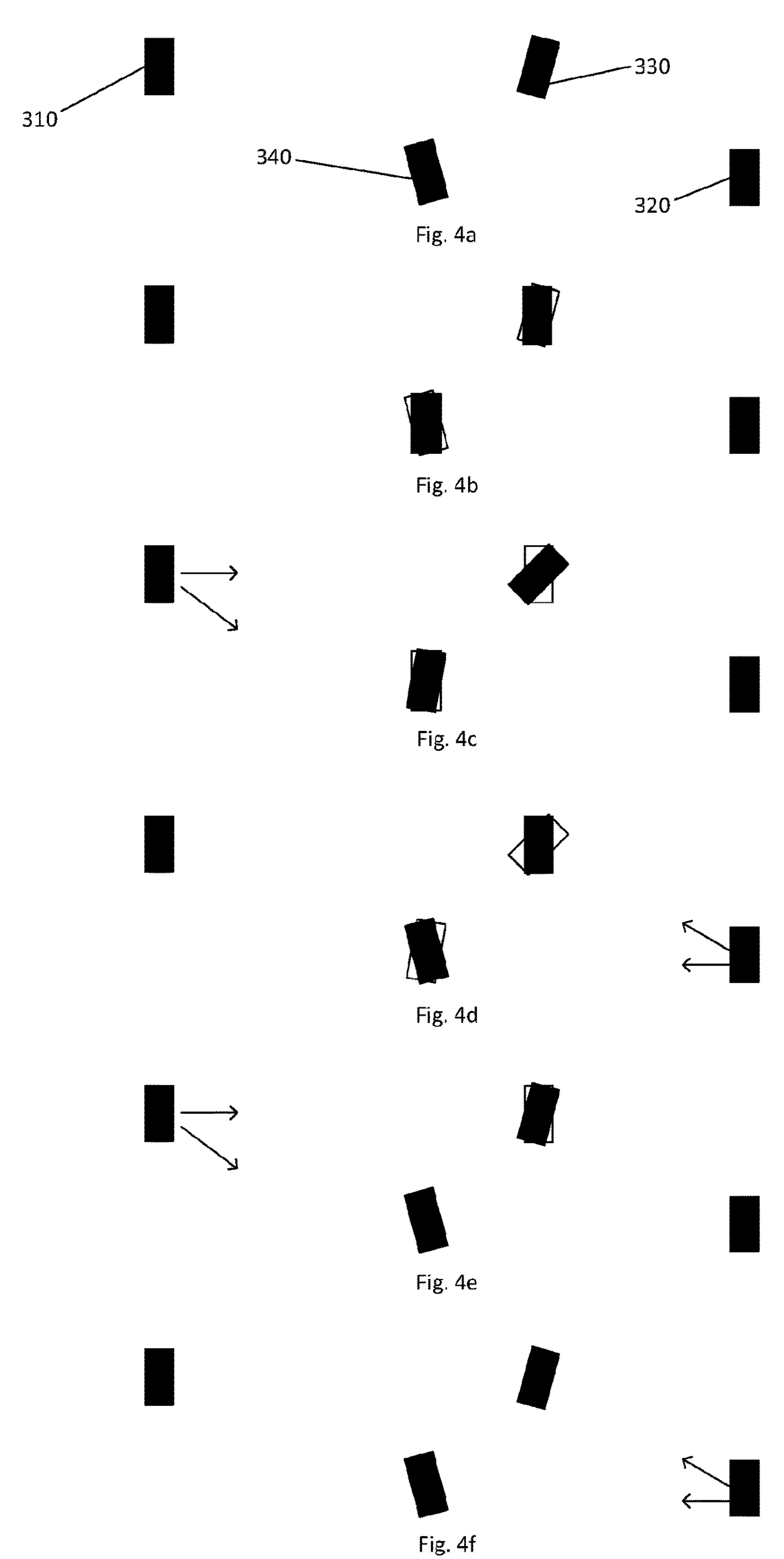

The arrangement of FIG. 4*a* is that of FIG. 3*e*, only the optical elements are now shown by black rectangles. The angles of the rectangles represent the angle which those rectangles may make to the surface of the scalp. As can be seen in FIG. 4*a*, both the first detector 330 and the second detector 340 are at an angle to the scalp (e.g. their scalp-facing surfaces will not be running parallel to the scalp).

FIGS. 4*b* to 4*f* show how these angles may be changed (e.g. to adjust the pitch of the optical elements). Again, the detectors are optimised to the sources. The black filled detector rectangles indicate new arrangements for the detectors, whereas the white filled detector rectangles indicate their previous arrangement.

In FIG. 4*b*, the two detectors are each aligned to provide a parallel arrangement with the scalp surface. For example, this may be as described above, such as through use of a sensor to obtain a measurement indicative of a capacitance or impedance associated with the scalp facing region of the detector and the scalp itself. FIG. 4*b* therefore shows the two detectors rearranged into an arrangement where their scalp facing region runs substantially parallel to the scalp surface in their region.

In some examples, the method may stop after FIG. 4*b*. For example, the arrangement of optical elements may be considered optimised with this parallel arrangement established. In other examples, the optimisation may also be based on detection performance for the different source-detector pairs. In which case, the step shown in FIG. 4*b* may be skipped, and the method may proceed to subsequent steps.

FIGS. 4*c* to 4*f* show steps of optimising the pitch of the first and second detectors relative to the first and second light sources. These four steps are similar to those shown in FIGS. 3*b* to 3*e*, only it is the detector pitch which is being varied. In some cases, it may be that varying the pitch of one or more of the optical elements (e.g. different to the parallel arrangement) provides improved performance. For example, the pitch of the detectors may be optimised to different light sources.

In FIG. 4*c*, the pitch of the first and second detectors is adjusted based on measurements for the first light source 310. This may involve an iterative optical element adjustment process in which light is emitted from the first light source 310, and each detector's pitch is adjusted until a suitable pitch is identified (similar to the process for adjusting the position of detectors with reference to FIG. 3*b*). As seen in FIG. 4*c*, the pitch of the detectors has changed so that their scalp facing surfaces are directed slightly towards the first light source 310.

In FIG. 4*d*, the pitch of the first and second detectors is adjusted based on measurements of the second light source 320. This may involve an iterative optical element adjustment process in which light is emitted from the second light source 320, and each detector's pitch is adjusted until a suitable pitch is identified (similar to the process for adjusting the position of detectors with reference to FIG. 3*c*). Measurements from the first light source 310 optimisation may be taken into account, so that the chosen pitch for each of the detectors is a compromised pitch chosen to provide a desired overall performance efficiency for both the first and second light sources. Again, this may include applying one or more weightings to the respective pairings, so that the compromised pitch is based also on an indication of which pairings are more important. As can be seen in FIG. 4*d*, the pitch angles of the two detectors have changed so that their scalp facing surfaces are now directed back towards the second light source 320 somewhat. The second light detector's pitch has changed quite a lot, and is quite biased in the direction of the second light source 320, as the second source-second detector pairing is more important than the first source-second detector pairing. The first light detector's pitch has also changed, and is in a relatively neutral pitch between the first and second light sources because neither of its two pairings are substantially more important than the other (e.g. to justify a biasing in favour of one over the other).

FIGS. 4*e* and 4*f* show additional stages in the iterative process. These may be validation stages in which the updated arrangement is tested for each light source. Further final changes in pitch may be provided. These will typically be much less significant than those in earlier steps of the method. As can be seen, in FIG. 4*e*, a small change in pitch is provided for the first detector 330 to improve its pitch relative to the first light source 310. In FIG. 4*f*, no further changes in pitch are provided, and the arrangement is ready for neuroimaging and analysis.

FIGS. 5*a* to 5*f* show exemplary steps of a method of arranging optical elements on a subject's scalp. In this method, the arrangement of sources is optimised for the detectors.

Figures 5A, 5B, 5C, 5D, 5E, 5F:
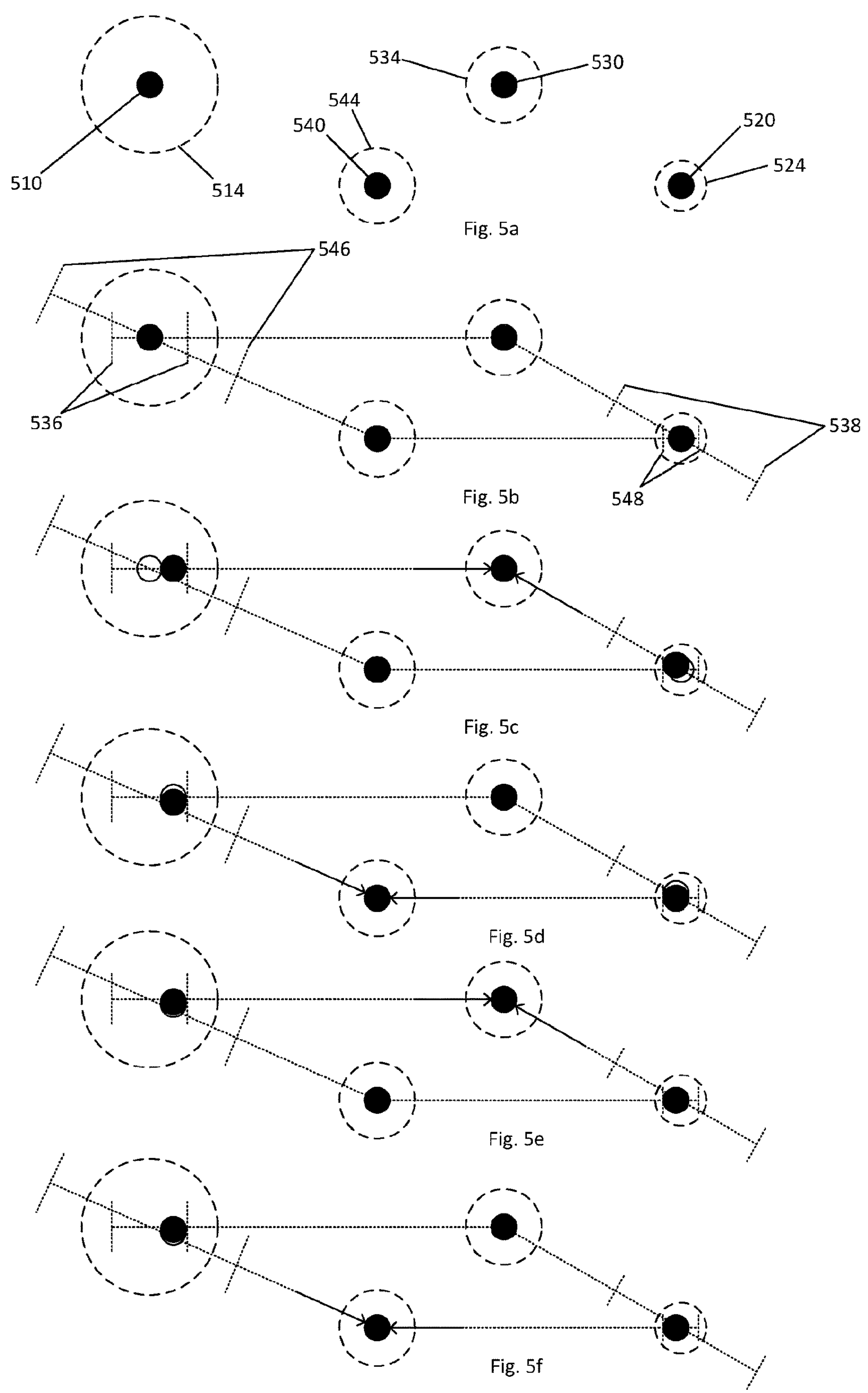

As shown in FIG. 5*a*, there is a first light source 510, a second light source 520, a first detector 530, and a second detector 540. Again, exemplary constraints are shown in FIGS. 5*a* and 5*b*. These include positional constraints for the location of optical elements on the subject's scalp and/or source-detector separation distance constraints for the different source-detector pairs. FIG. 5*a* shows position constraints including a first light source allowable region 514, a second light source allowable region 524, a first light detector allowable region 534, and a second light detector allowable region 544. FIG. 5*b* shows source-detector separation distance constraints including a first detector-first source allowable separation distance range 536, a second detector-first source allowable separation distance range 546, a first detector-second source allowable separation distance range 538, and a second detector-second source allowable separation distance range 548.

FIGS. 5*c* to 5*e* show steps in re-arranging the optical elements on the subject's scalp. Instead of optimising detector location for each source, the method involves optimising source location for each detector. In FIGS. 5*c* and 5*e*, optimisation is performed based on the first detector 530, and in FIGS. 5*b* and 5*f*, optimisation is performed based on the second detector 540. The steps of determining how to adjust the source positions are similar to those described above in relation to adjusting detector positions, and so will not be described again here. As can be seen from these Figs., the positioning of the two sources may be adjusted to provide an overall performance metric which satisfies a threshold criterion. In this example, movement of the second source 520 is limited due to precise constraints on its location, and/or due to precise separation distance constraints. Again, performance of the second detector-second source coupling is prioritised when optimising the individual source locations.

The above methods may be used interchangeably. For example, both sources and detectors may be optimised in the same method. One optimisation may happen after the other, or the two may occur interchangeably (e.g. optimise first source 510, first detector 530, second source 520, second detector 540, and optionally repeat). Likewise, adjusting tilt may occur in between steps of adjusting position of source and/or detector. Tilt adjustment may be performed for sources and/or for detectors (e.g. the tilt of light sources may be adjusted to improve performance with detectors).

As described above, the arrangement of optical elements on the subject's scalp may be optimised to provide improved operation of the neuroimaging system. This arrangement of optical elements may be optimised subject to one or more constraints. Exemplary constraints described above include positional constraints for allowable positions of optical elements on the subject's scalp, and/or source-detector separation distance constraints. Additionally, or alternatively, other factors may be utilised when optimising the arrangement of optical elements on the subject's scalp. For example, constraints may not be specific to any one optical element. Instead, constraints may apply to a plurality of elements and/or regions of the scalp.

As one example, the density of optical elements on the scalp may be considered. In which case, the exact position of an optical element need not fall within a specified range for that optical element, but instead, there may need to be a threshold number of optical elements within a selected region of the scalp (e.g. the optical element density may have to be above a threshold for the scalp or sub-regions of the scalp). The arrangement of optical elements may then be adjusted to improve performance of the system while ensuring that sufficient optical element density remains for a particular region of the scalp. The scalp may be divided into a plurality of sub-regions, and one or more (e.g. all) of the sub-regions may have a respective density requirement associated therewith. For example, some sub-regions may have higher density requirements than other sub-regions.

Constraints may be updated on-the-fly. For example, constraints for individual optical elements may be dependent on performance characteristics of other optical elements in the arrangement. Optical elements may be optimised sequentially. Where there are a large number of optical elements, some of the later elements to be optimised may be adaptively deemed less important. For example, constraints for one optical element may be selected based at least in part on established operational parameters for its neighbouring elements. As one example, the requirements for one detector to be particularly optimised in relation to one source may be reduced if that one detector has one or more neighbouring detectors which have already been optimised (e.g. and which have resulted in high quality values being obtained for those neighbouring detectors). For example, threshold criteria may comprise global criteria designed so that the optimisation of optical elements within one sub-region (or for the scalp as a whole) satisfies a threshold criteria (even if individual optical elements within that region do not perform to such a high standard).

Embodiments of the present disclosure may provide an automated system for performing such optimisations. The automated system may comprise an actuator including a plurality of movers. The actuator may form part of the neuroimaging system, or it may be a separate component arranged to interact with such a neuroimaging system.

The actuator comprises a plurality of movers, where each mover is operable to adjust the arrangement of one or more optical elements on a subject's scalp. That is, each mover may be operable to adjust the position of an optical element, and/or it may be operable to adjust the tilt of an optical element. The actuator may be arranged so that the movers may be positioned in contact with, or proximal to, some or all of the optical elements of the neuroimaging system. For example, the actuator may have a plurality of optical element receiving sections located adjacent to the movers. The actuator may be positioned with the optical elements in the optical element receiving sections, and the movers may be actuated to control the arrangement of the optical elements on the scalp.

The movers may comprise suitable components for moving the optical elements on the subject's scalp. For example, movers may comprise one or pumps, such as hydraulic or pneumatic pumps arranged to selectively apply pressure to an optical element to provide movement thereof. For example, movers may comprise one or more motors. Motors may be configured to provide selective movement of the optical elements in response to an actuation signal. For example, movers may utilise magnetic field-based movement solutions. Such movers may comprise an electromagnet (such as a solenoid), which may selectively apply current to generate a magnetic field to cause movement of the optical elements.

The movers may be configured to selectively apply force/pressure to different regions of the optical elements and/or from different directions. One or more movers may be used to control the positioning of an optical element (e.g. by applying force to the optical element in one of a plurality of different directions to move the optical element in a given direction). One or more movers may be used to control the tilt of an optical element (e.g. by applying force to a particular region of the optical element to provide tilting/pivoting of the element). For example, multiple movers may apply a force to an optical element to control the directionality of its movement and/or its tilting. For example, a body of each optical element may extend away from its scalp-facing surface. The body may comprise a wire and/or may be part of a main region of the optical element. The movers may be arranged to move the body to provide desired movement, e.g. by moving the angle of the wire, the tilt of the element may be changed.

The actuator may comprise one or more contact sensor, such as an electrical sensor for sensing an indication of a contact property (e.g. impedance or capacitance). The sensor may enable measurements to be obtained which indicated whether or not the optical element is arranged in a parallel arrangement with the scalp.

The actuator may comprise a scalp contacting surface for placing on the subject's scalp. Where the actuator is a separate component to the rest of the neuroimaging system, the actuator may comprise coupling means for attaching the actuator to the neuroimaging system. The actuator may be arranged in a fixed position relative to the neuroimaging system. The actuator may provide a fixed frame of reference for movement of the optical elements of the neuroimaging system. The actuator may therefore be configured to be placed on the subject's scalp (and coupled to the neuroimaging system, where relevant), and configured to selectively re-arrange some or all of the optical elements of the neuroimaging system on the subject's scalp.

The actuator may comprise a data store and a processor. The processor may be coupled to the data store to obtain data therefrom and/or to write data to the data store. The actuator may be configured to couple to the optical elements of the neuroimaging system to control operation thereof and/or to obtain measurement data therefrom. The processor may be configured to control operation of the plurality of optical elements to implement the arrangement methods disclosed herein. For example, the processor may be configured to control operation of sources to selectively emit light for detection by the detectors, and to determine metrics for the detectors based on light detected by said detectors. The processor may then be configured to control operation of one or more of the movers to adjust the arrangement of one or more of the optical elements as described herein. The data store may store data relating to the process. For example, the data store may store data indicative of one or more of the constraints to be applied during the arrangement process (e.g. allowable position data, allowable source-detector separation data, density requirements, sub-region definitions and requirements etc.). The actuator may therefore be arranged to implement methods described herein automatically (e.g. once programmed with relevant constraints). The actuator may be coupled to a user input device to enable user control of one or more properties of the actuator.

It will be appreciated from the discussion above that the examples shown in the figures are merely exemplary, and include features which may be generalised, removed or replaced as described herein and as set out in the claims. With reference to the drawings in general, it will be appreciated that schematic functional block diagrams are used to indicate functionality of systems and apparatus described herein. In addition, the processing functionality may also be provided by devices which are supported by an electronic device. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some examples the function of one or more elements shown in the drawings may be integrated into a single functional unit.

As will be appreciated by the skilled reader in the context of the present disclosure, each of the examples described herein may be implemented in a variety of different ways. Any feature of any aspects of the disclosure may be combined with any of the other aspects of the disclosure. For example method aspects may be combined with apparatus aspects, and features described with reference to the operation of particular elements of apparatus may be provided in methods which do not use those particular types of apparatus. In addition, each of the features of each of the examples is intended to be separable from the features which it is described in combination with, unless it is expressly stated that some other feature is essential to its operation. Each of these separable features may of course be combined with any of the other features of the examples in which it is described, or with any of the other features or combination of features of any of the other examples described herein. Furthermore, equivalents and modifications not described above may also be employed without departing from the invention.

Certain features of the methods described herein may be implemented in hardware, and one or more functions of the apparatus may be implemented in method steps. It will also be appreciated in the context of the present disclosure that the methods described herein need not be performed in the order in which they are described, nor necessarily in the order in which they are depicted in the drawings. Accordingly, aspects of the disclosure which are described with reference to products or apparatus are also intended to be implemented as methods and vice versa. The methods described herein may be implemented in computer programs, or in hardware or in any combination thereof. Computer programs include software, middleware, firmware, and any combination thereof. Such programs may be provided as signals or network messages and may be recorded on computer readable media such as tangible computer readable media which may store the computer programs in non-transitory form. Hardware includes computers, handheld devices, programmable processors, general purpose processors, application specific integrated circuits (ASICs), field programmable gate arrays (FPGAs), and arrays of logic gates. Any controller described herein may be provided by any control apparatus such as a general purpose processor configured with a computer program product configured to program the processor to operate according to any one of the methods described herein. In addition, the functionality of the controller may be provided by an application specific integrated circuit, ASIC, or by a field programmable gate array, FPGA, or by a configuration of logic gates, or by any other control apparatus. For example, a controller may be used to implement methods described herein, and/or methods may be implemented using analogue circuitry.

Other examples and variations of the disclosure will be apparent to the skilled addressee in the context of the present disclosure.

The specification can be understood with reference the following Numbered Paragraphs:

Numbered Paragraph 1. A method of preparing a neuroimaging system for neuroimaging and analysis of a subject's brain tissue, the neuroimaging system comprising a plurality of optical elements, wherein each optical element comprises one of: (i) a light source for emitting light towards the subject's brain tissue, or (ii) a light detector for detecting scattered light from the subject's brain tissue, the method comprising:

placing optical elements on the subject's scalp to provide at least one source-detector pair where a light source on the subject's scalp is arranged to emit light towards the subject's brain tissue and a detector on the subject's scalp is arranged to detect scattered light from the subject's brain tissue which was emitted from that light source;

wherein placing an optical element on the subject's scalp comprises:

first, arranging said optical element at a selected location on the subject's scalp for providing at least one source-detector pair; and then, performing an iterative optical element arrangement adjustment process comprising:

obtaining a measurement signal indicative of a goodness of fit for said optical element as arranged on the subject's scalp; and re-arranging said optical element at, or proximal to, the selected location on the subject's scalp based on the indication of goodness of fit for said optical element;

wherein said iterative optical element arrangement adjustment process is repeated until a said measurement signal indicates a goodness of fit for said optical element which satisfies a threshold criterion.

Numbered Paragraph 2. The method of Numbered Paragraph 1, wherein obtaining a measurement signal indicative of a goodness of fit for an optical element of a source-detector pair comprises: (i) controlling the light source of the pair to emit a reference light signal, and (ii) controlling the detector of the pair to obtain a reference light detection signal; and wherein said measurement signal indicative of goodness of fit for said optical element of the source-detector pair is based on the reference light detection signal.

Numbered Paragraph 3. The method of Numbered Paragraph 2, wherein said measurement signal indicative of goodness of fit for said optical element is based on a signal-to-noise ratio for the reference light signal as identifiable in the reference light detection signal.

Numbered Paragraph 4. The method of Numbered Paragraph 3, wherein satisfying the threshold criterion comprises said signal-to-noise ratio being greater than a signal threshold value.

Numbered Paragraph 5. The method of any preceding Numbered Paragraph, wherein obtaining a said measurement signal for a said optical element comprises using a sensor to obtain an indication of a property indicating an angular offset between the optical element and the subject's scalp.

Numbered Paragraph 6. The method of Numbered Paragraph 5, wherein the sensor comprises a capacitance sensor configured to sense a capacitance associated with the optical element and/or the subject's scalp; and wherein satisfying the threshold criterion comprises sensing a capacitance greater than a capacitance threshold value.

Numbered Paragraph 7. The method of Numbered Paragraph 5 or 6, wherein the sensor comprises an impedance sensor configured to sense an impedance associated with the optical element and/or the subject's scalp, for example wherein the impedance sensor is an RF impedance sensor; and wherein satisfying the threshold criterion comprises sensing an impedance below an impedance threshold value.

Numbered Paragraph 8. The method of any preceding Numbered Paragraph, wherein re-arranging a said optical element comprises adjusting the pitch of the optical element relative to the subject's scalp and/or translating the optical element to a different location on the subject's scalp.

Numbered Paragraph 9. The method of Numbered Paragraph 8, wherein each optical element comprises: (i) a scalp facing region for facing the scalp, and (ii) a body extending away from the scalp facing region; and wherein adjusting the pitch of a said optical element relative to the subject's scalp comprises changing the pitch of the body of said optical element relative to the subject's scalp.

Numbered Paragraph 10. The method of any preceding Numbered Paragraph, wherein the threshold criterion for a said optical element is selected based on a goodness of fit for one or more other optical elements arranged on the subject's scalp, for example wherein the threshold criterion for each said optical element is selected so that a global goodness of fit for the plurality of optical elements as a whole is greater than a global threshold value.

Numbered Paragraph 11. The method of Numbered Paragraph 10, wherein the optical elements are placed on the subject's scalp to provide a plurality of source-detector pairs, wherein at least one optical element on the subject's scalp is part of more than one source-detector pair, and wherein the threshold criterion for said at least one optical element is selected based on the other optical elements in its source detector pairs.

Numbered Paragraph 12. The method of any preceding Numbered Paragraph, wherein an amount and/or direction of re-arranging for a said optical element is selected based on the indication of the goodness of fit for said optical element, for example wherein the amount and/or direction of re-arranging for a said optical element is selected based on a difference between the indication of goodness of fit in a said measurement signal and the goodness of fit which satisfies the threshold criterion.

Numbered Paragraph 13. The method of any preceding Numbered Paragraph, wherein at least one of:

the threshold criterion for a said optical element is selected based on the selected location for said optical element;

the threshold criterion for a said optical element is selected based on a determined goodness of fit for other optical elements proximal to said optical element;

each of the plurality of optical elements is placed on the subject's scalp prior to any iterative optical element arrangement adjustment process occurring; and the neuroimaging system for neuroimaging and analysis of a subject's brain tissue comprises an EROS system and/or an fNIRS system.

Numbered Paragraph 14. The method of any preceding Numbered Paragraph, wherein the iterative optical element arrangement adjustment process is performed automatically using a mechanical actuator configured to obtain each said measurement signal and to rearrange each said optical element in response to a said measurement signal indicating the goodness of fit for said optical element does not satisfy the threshold criterion.

Numbered Paragraph 15. A method of neuroimaging and analysing a subject's brain tissue using a neuroimaging system, the method comprising preparing the neuroimaging system as defined in any of Numbered Paragraphs 1 to 14, and controlling operation of the neuroimaging system to provide neuroimaging and analysis of the subject's brain tissue.

Numbered Paragraph 16. An actuator configured to prepare a neuroimaging system for neuroimaging and analysis of a subject's brain tissue, wherein the neuroimaging system comprises a plurality of optical elements, wherein each optical element comprises one of: (i) a light source for emitting light towards the subject's brain tissue, or (ii) a light detector for detecting scattered light from the subject's brain tissue, wherein:

the actuator comprises a plurality of movers, wherein each mover is operable to rearrange one or more optical elements of said neuroimaging system;

the actuator is arranged to couple to said neuroimaging system to position the movers proximal to, or in contact with, said optical elements of said neuroimaging system; and the actuator is configured to control operation of each of the movers to re-arrange said optical elements on the subject's scalp.

Numbered Paragraph 17. The actuator of Numbered Paragraph 16, wherein each said optical element of said neuroimaging system comprises: (i) a scalp facing region for facing the scalp, and (ii) a body extending away from the scalp facing region; and wherein each mover is arranged to move said body relative to the subject's scalp to provide rearrangement of said optical element on the subject's scalp.

Numbered Paragraph 18. The actuator of Numbered Paragraph 17, wherein the actuator is configured to control operation of each mover to move the body of said optical element to adjust a pitch of said optical element relative to the subject's scalp.

Numbered Paragraph 19. The actuator of any of Numbered Paragraphs 16 to 18, further comprising at least one contact sensor configured to sense an indication of a contact property for contact between a said optical element and the subject's scalp.

Numbered Paragraph 20. The actuator of Numbered Paragraph 19, wherein the contact sensor comprises at least one of: (i) a capacitance sensor configured to sense a capacitance associated with said optical element and/or the subject's scalp, and (ii) an impedance sensor configured to sense an impedance associated with said optical element and/or the subject's scalp.

Numbered Paragraph 21. The actuator of any of Numbered Paragraphs 16 to 20, wherein the actuator is configured to control operation of the one or more movers to perform an iterative optical element arrangement adjustment process for each of said optical elements arranged at respective selected locations on the subject's scalp;

wherein, to perform said iterative optical element arrangement adjustment process for a light source and/or light detector of a source-detector pair on the patient's scalp, the actuator is configured to:

(a) obtain a measurement signal indicative of a goodness of fit for said optical element as arranged on the subject's scalp;

(b) control operation of one or more of the movers to re-arrange said optical element at, or proximal to, its selected location on the subject's scalp; and (c) repeat steps (a) and (b) until a said measurement signal is obtained which indicates a goodness of fit for said optical element which satisfies a threshold criterion.

Numbered Paragraph 22. The actuator of Numbered Paragraph 21, wherein at least one optical element is part of more than one source-detector pair, and wherein the actuator is configured to perform the optical element arrangement adjustment process for said optical element until a threshold criterion is satisfied for that optical element in each of its plurality of source-detector pairs.

Numbered Paragraph 23. A neuroimaging system comprising:

a plurality of optical elements comprising: (i) one or more light sources for emitting light towards a subject's brain tissue; and (ii) one or more light detectors for detecting scattered light from the subject's brain tissue; and an actuator operable to prepare the optical elements of the neuroimaging system for neuroimaging and analysis of the subject's brain tissue.

Numbered Paragraph 24. The neuroimaging system of Numbered Paragraph 23, wherein the actuator comprises an actuator as defined in any of Numbered Paragraphs 16 to 22.

Numbered Paragraph 25. A computer program product comprising computer program instructions configured to program a controller to perform the method of any of Numbered Paragraphs 1 to 15.

The invention claimed is:

1. A method of preparing a system for analysis of a subject's brain tissue, the system comprising a plurality of optical elements, wherein each optical element comprises one of: (i) a light source for emitting light towards the subject's brain tissue, or (ii) a light detector for detecting scattered light from the subject's brain tissue, the method comprising:

placing two of the plurality of optical elements on the subject's scalp to provide a source-detector pair in which a light source of the source-detector pair at a first position on the subject's scalp is arranged to emit light towards the subject's brain tissue and a light detector of the source-detector pair at a second position on the subject's scalp is arranged to detect scattered light from the subject's brain tissue which was emitted from the light source of the source-detector pair;

wherein placing an optical element of the two optical elements on the subject's scalp comprises:

first, arranging said optical element at a selected location on the subject's scalp for providing the at least one source-detector pair; and then, performing an iterative optical element arrangement adjustment process comprising:

obtaining a measurement signal indicative of a goodness of fit for said optical element as arranged on the subject's scalp by (i) controlling the light source of the source-detector pair to emit a reference light signal, and (ii) controlling the light detector of the source-detector pair to obtain a reference light detection signal, wherein the measurement signal is based on the reference light detection signal; and re-arranging said optical element at, or proximal to, the selected location on the subject's scalp based on the indication of goodness of fit for said optical element;

wherein said iterative optical element arrangement adjustment process is repeated until the measurement signal indicates a goodness of fit for said optical element which satisfies a threshold criterion;

wherein said iterative optical element arrangement adjustment process is performed automatically using a mechanical actuator configured to re-arrange each said optical element in response to the measurement signal indicating the goodness of fit for said optical element does not satisfy the threshold criterion.

2. The method of claim 1, wherein said measurement signal indicative of goodness of fit for said optical element is based on a signal-to-noise ratio for the reference light signal as identifiable in the reference light detection signal.

3. The method of claim 2, wherein satisfying the threshold criterion comprises said signal-to-noise ratio being greater than a signal threshold value.

4. The method of claim 1, wherein obtaining the measurement signal for the optical element comprises using a sensor to obtain an indication of a property indicating an angular offset between the optical element and the subject's scalp.

5. The method of claim 4, wherein the sensor comprises a capacitance sensor configured to sense a capacitance associated with the optical element and/or the subject's scalp; and wherein satisfying the threshold criterion comprises sensing a capacitance greater than a capacitance threshold value.

6. The method of claim 4, wherein the sensor comprises an impedance sensor configured to sense an impedance associated with the optical element and/or the subject's scalp; and wherein satisfying the threshold criterion comprises sensing an impedance below an impedance threshold value.

7. The method of claim 1, wherein re-arranging the optical element comprises adjusting the pitch of the optical element relative to the subject's scalp and/or translating the optical element to a different location on the subject's scalp.

8. The method of claim 1, wherein the threshold criterion for the optical element is selected based on a goodness of fit for one or more other optical elements arranged on the subject's scalp.

9. The method of claim 8, wherein the optical elements are placed on the subject's scalp to provide a plurality of source-detector pairs, wherein at least one optical element on the subject's scalp is part of more than one source-detector pair, and wherein the threshold criterion for said at least one optical element is selected based on the other optical elements in its source detector pairs.

10. The method of claim 1, wherein an amount and/or direction of re-arranging for the optical element is selected based on the indication of the goodness of fit for said optical element.

11. The method of claim 1, wherein:

the actuator comprises a plurality of movers, wherein each mover is operable to rearrange one or more optical elements of said system;

the actuator is arranged to couple to said system to position the movers proximal to, or in contact with, said optical elements of said system; and the actuator is configured to control operation of each of the movers to re-arrange said optical elements on the subject's scalp.

12. An actuator configured to prepare a system for analysis of a subject's brain tissue, wherein the system comprises a plurality of optical elements, wherein each optical element comprises one of: (i) a light source for emitting light towards the subject's brain tissue, or (ii) a light detector for detecting scattered light from the subject's brain tissue, wherein:

the actuator comprises a plurality of movers, wherein each mover is operable to rearrange one or more optical elements of said system;

the actuator is arranged to couple to said system to position the movers proximal to, or in contact with, said optical elements of said system; and the actuator is configured to control operation of each of the movers to re-arrange said optical elements on the subject's scalp;

wherein the actuator is configured to control operation of the one or more movers to perform an iterative optical element arrangement adjustment process for each of said optical elements arranged at respective selected locations on the subject's scalp;

wherein, to perform said iterative optical element arrangement adjustment process for a light source and/or light detector of a source-detector pair on the patient's scalp, the actuator is configured to:

(a) obtain a measurement signal indicative of a goodness of fit for said optical element as arranged on the subject's scalp by (i) controlling the light source of the pair to emit a reference light signal, and (ii) controlling the light detector of the pair to obtain a reference light detection signal, wherein the measurement signal is based on the reference light detection signal;

(b) control operation of one or more of the movers to re-arrange said optical element at, or proximal to, its selected location on the subject's scalp; and (c) repeat steps (a) and (b) until the measurement signal is obtained which indicates a goodness of fit for said optical element which satisfies a threshold criterion.

13. The actuator of claim 12, wherein each said optical element of said system comprises: (i) a scalp facing region for facing the scalp, and (ii) a body extending away from the scalp facing region; and wherein each mover is arranged to move said body relative to the subject's scalp to provide rearrangement of said optical element on the subject's scalp.

14. The actuator of claim 13, wherein the actuator is configured to control operation of each mover to move the body of said optical element to adjust a pitch of said optical element relative to the subject's scalp.

15. The actuator of claim 12, further comprising at least one contact sensor configured to sense an indication of a contact property for contact between the optical element and the subject's scalp.

16. The actuator of claim 12, wherein at least one optical element is part of more than one source-detector pair, and wherein the actuator is configured to perform the optical element arrangement adjustment process for said optical element until a threshold criterion is satisfied for that optical element in each of its plurality of source-detector pairs.

17. A tangible non transitory computer readable storage medium storing program instructions configured, when executed by a computer to cause the computer to perform a method comprising:

performing an iterative optical element arrangement adjustment process comprising:

obtaining a measurement signal indicative of a goodness of fit for a selected optical element of a source detector pair as arranged on a subject's scalp by:

(i) controlling the light source of the source-detector pair at a first position on the subject's scalp to emit a reference light signal, and (ii) controlling the light detector of the source-detector pair at a second position on the subject's scalp to obtain a reference light detection signal, wherein the measurement signal is based on the reference light detection signal;

wherein the source-detector pair is provided by two optical elements placed on the subject's scalp and a first one of said two optical elements comprises a light source for emitting light towards the subject's brain tissue and a second one of said two optical elements comprising a light detector for detecting scattered light from the subject's brain tissue, and determining, based on the measurement signal, whether to cause the selected optical element to be rearranged at, or proximal to, the selected location on the subject's scalp;

and, once the selected optical element has been rearranged, repeating the steps of obtaining the measurement signal and determining, based on the measurement signal, whether to cause the selected optical element to be rearranged until the measurement signal indicates a goodness of fit for said optical element which satisfies a threshold criterion.

* * * * *